US011840735B2

(12) United States Patent
Meves et al.

(10) Patent No.: US 11,840,735 B2
(45) Date of Patent: Dec. 12, 2023

(54) METHODS AND MATERIALS FOR IDENTIFYING MALIGNANT SKIN LESIONS

(71) Applicant: Mayo Foundation for Medical Education and Research, Rochester, MN (US)

(72) Inventors: Alexander Meves, Rochester, MN (US); Ekaterina M. Nikolova, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/518,783

(22) Filed: Jul. 22, 2019

(65) Prior Publication Data

US 2019/0338372 A1 Nov. 7, 2019

Related U.S. Application Data

(63) Continuation of application No. 14/442,673, filed as application No. PCT/US2013/053982 on Aug. 7, 2013, now abandoned.

(60) Provisional application No. 61/726,217, filed on Nov. 14, 2012.

(51) Int. Cl.
*C07H 21/04* (2006.01)
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,695,913 B2 * | 4/2010 | Cowens | C12Q 1/6886 435/6.14 |
| 2004/0010045 A1 | 1/2004 | Yi | |
| 2004/0110221 A1 * | 6/2004 | Twine | C12Q 1/6886 435/6.11 |
| 2006/0235001 A1 | 10/2006 | Elliott et al. | |
| 2007/0154889 A1 | 7/2007 | Wang | |
| 2008/0274908 A1 | 11/2008 | Chang | |
| 2009/0125247 A1 | 5/2009 | Baker et al. | |
| 2010/0028876 A1 | 2/2010 | Gordon et al. | |
| 2011/0123997 A1 | 5/2011 | Kashani-Sabet et al. | |
| 2011/0159496 A1 | 6/2011 | Kashani-Sabet et al. | |
| 2012/0071343 A1 | 3/2012 | Ma et al. | |
| 2012/0128667 A1 | 5/2012 | Chow et al. | |
| 2014/0045915 A1 | 2/2014 | Skog et al. | |
| 2015/0290289 A1 | 10/2015 | Sampath | |
| 2016/0115555 A1 | 4/2016 | Ma et al. | |
| 2016/0222457 A1 | 8/2016 | Meves et al. | |
| 2017/0275700 A1 | 9/2017 | Meves et al. | |

FOREIGN PATENT DOCUMENTS

| | | |
|---|---|---|
| WO | 2014/077915 A1 | 5/2014 |
| WO | 2016/025717 A1 | 2/2016 |
| WO | 2017/196944 | 11/2017 |

OTHER PUBLICATIONS

NEB catalog (1998/1999), pp. 121, 284. (Year: 1998).*
(Annex 1) American Cancer Society"Treatment of Melanoma Skin Cancer, by Stage" 4 pages, accessed Nov. 19, 2020, https://www.cancer.org/cancer/melanoma-skin-cancer/treating/by-stage.html.
(American Joint Committee on Cancer) AJCC Cancer Staging Manual. Technical Manual [online]. 2002 [Retrieved on Jul. 28, 2017]. Retrieved from the Internet: <URL: https://cancerstaging.org/references-tools/deskreferences/Documents/AJCC6thEdCancerStagingManualPart2.pdf>; p. 209, Summary of Changes.
(Meves, A et al.) Tumor Cell Adhesion as a Risk Factor for Sentinel Lymph Node Metastasis in Primary Cutaneous Melanoma. Journal of Clinical Oncology. Aug. 10, 2015, vol. 33, No. 23; pp. 2509-2515; abstract; p. 2510, 1st column, 3rd paragraph; p. 2511, 2nd column, 4th paragraph; p. 2513, 2nd column, 2nd paragraph; Table 3.
Anders and Huber, "Differential expression analysis for sequence count data," Genome Biol., 11(10):R106, Epub Oct. 27, 2010.
Balch et al., "Final version of 2009 AJCC melanoma staging and classification," J Clin Oncol., 27(36):6199-6206, Epub Nov. 16, 2009.
Balch et al., "Sentinel node biopsy and standard of care for melanoma," J Am Acad Dermatol., 60(5):872-875, May 2009.
Benjamin et al., "p53 and the Pathogenesis of Skin Cancer", Toxicol Appl Pharmacol., Nov. 1, 2007; vol. 224 No. 3, pp. 241-248 (available in PMC Nov. 1, 2008, pp. 1-13), especially abstract, p. 2, 3rd para, p. 3, 2nd para, p. 4, last para, p. 7, last para-p. 8, 1st para.
Bernard et al., "Use of a new bioassay to study pentamidine pharmacokinetics," J Infect Dis., 152(4):750-754, Oct. 1985.
Breslow, "Thickness, cross-sectional areas and depth of invasion in the prognosis of cutaneous melanoma," Ann Surg., 172(5):902-908, Nov. 1970.
Bullard et al., "Evaluation of statistical methods for normalization and differential expression in mRNA-Seq experiments," BMC Bioinformatics 11:94, Feb. 18, 2010.

(Continued)

*Primary Examiner* — Jeanine A Goldberg
(74) *Attorney, Agent, or Firm* — TraskBritt

(57) ABSTRACT

This document provides methods and materials for identifying malignant skin lesions (e.g., malignant pigmented skin lesions). For example, methods and materials for using quantitative PCR results and correction protocols to reduce the impact of basal keratinocyte contamination on the analysis of test sample results to identify malignant skin lesions are provided.

2 Claims, 5 Drawing Sheets
Specification includes a Sequence Listing.

(56) References Cited

OTHER PUBLICATIONS

Carlson et al., "Establishment, maintenance and in vitro and in vivo applications of primary human glioblastoma multiforme (GBM) xenograft models for translational biology studies and drug discovery," Curr Protoc Pharmacol., Chapter 14:Unit 14.16, Mar. 2011.
Chan et al., "Regulation of adhesion dynamics by calpain-mediated proteolysis of focal adhesion kinase (FAK)," J Biol Chem., 285(15):11418-11426, Epub Feb. 11, 2010.
ClinicalTrials.gov Identifier: NCT00729807, "Pentamidine in Treating Patients With Relapsed or Refractory Melanoma," ClinicalTrials.gov [online] 2008 [retrieved on Mar. 26, 2015]. Retrieved from the Internet: <URL: https://www.clinicaltrials.gov/ct2/show/NCT00729807?term=NCT00729807&rank=1>, 4 pages.
Conway et al., "Gene expression profiling of paraffin-embedded primary melanoma using the DASL assay identifies increased osteopontin expression as predictive of reduced relapse-free survival," Clin Cancer Res., 15(22):6939-6946, Epub Nov. 3, 2009.
Coppe et al., "Senescence-associated secretory phenotypes reveal cell-nonautonomous functions of oncogenic RAS and the p53 tumor sunnressor," PLoS Biol., 6(12):2853-2868, Dec. 2, 2008.
Hartman et al., "The Evolution of S100B Inhibitors for the Treatment of Malignant Melanoma", Future medicinal chemistry, Jan. 2013, vol. 5, No. 1, pp. 97-109. (available in PMC. Web pp. 1-25), especially abstract, p. 5, 2nd para, p. 7, last para-p. 8, 1st par.
Infante JR et al., "Safety, pharmacokinetic, and pharmacodynamic phase I dose-escalation trial of PF-00562271, an inhibitor of focal adhesion kinase, in advanced solid tumors," J Clin Oncol., 30(13):1527-1533, Epub Mar. 26, 2012.
International Search Report and Written Opinion for PCT/US2013/053982, dated Dec. 5, 2013, 5 pages.
Kashani-Sabet et al., "A multi-marker assay to distinguish malignant melanomas from benign nevi," Proc Natl Acad Sci U S A., 106(15):6268-6272, Epub Mar. 30, 2009.
King et al. Gene Expression Profile Analysis by DNA Microarrays. JAMA 2001, vol. 286, No. 18, pp. 2280-2288 (Year: 2001).
Lee et al., "The novel combination of chlorpromazine and pentamidine exerts synergistic antiproliferative effects through dual mitotic action," Cancer Res., 67(23):11359-11367, Dec. 1, 2007.
Meves et al., "Beta1 integrin cytoplasmic tyrosines promote skin tumorigenesis independent of their phosphorylation," Proc Natl Acad Sci U S A., 108(37):15213-15218, Epub Aug. 29, 2011.
Mitra et al., "Melanoma sentinel node biopsy and prediction models for relapse and overall survival," Br J Cancer., 103(8):1229-1236, Epub Sep. 21, 2010.
Pathak et al., "Pentamidine is an inhibitor of PRL phosphatases with anticancer activity," Mol Cancer Ther., 1(14):1255-1264, Dec. 2002.
Ruczinski et al., "Logic regression," Journal of Computational and Graphical Statistics, 12(3):475-511, 2003.
Sanovic et al., "Time-resolved gene expression profiling of human squamous cell carcinoma cells during the apoptosis process induced by photodynamic treatment with hypericin," Int. J. Oncol., 35(4):921-39, Oct. 2009.
Seo et al., "The effect of substrate microtopography on focal adhesion maturation and actin organization via the RhoA/ROCK pathway," Biomaterials., 32(36):9568-9575, Epub Sep. 16, 2011.
Siiskonen et al., "Chronic UVR causes increased immunostaining of CD44 and accumulation of hyaluronan in mouse epidermis," J Histochem Cytochem., 59(10):908-917, Epub Aug. 10, 2011.
Simon et al., "Expression of CD44 isoforms in human skin cancer," Eur J Cancer., 32A(8):1394-1400, Jul. 1996.
Smith et al., "The effect of pentamidine on melanoma ex vivo," Anticancer Drugs, 21(2):181-185, Feb. 2010.
Sun and Zhang, "Pentamidine binds to tRNA through non-specific hydrophobic interactions and inhibits aminoacylation and translation," Nucleic Acids Res., 36(5):1654-1664, Mar. 2008.
Sun Yang et al. Overabundance of Putative Cancer Stem Cells in Human Skin Keratinocyte Cells Malignantly Transformed by Arsenic. Toxicol Sci, Jan. 2012, 125(1), pp. 20-29. Published online Oct. 19, 2011. doi: 10.1093/toxsci/kfr282, pp. 1-11.
Talantov et al., "Novel genes associated with malignant melanoma but not benign melanocytic lesions," Clin Cancer Res., 11(20):7234-7242, Oct. 15, 2005.
Waalkes et al., "Pentamidine: clinical pharmacologic correlations in man and mice," Clin Pharmacol Ther., 11(4):505-512, Jul.-Aug. 1970.
Warters et al., "Differential gene expression in primary human skin keratinocytes and fibroblasts in response to ionizing radiation," Radiat Res., 172(1):82-95, Jul. 2009.
Whelan et al., "A method for the absolute quantification of cDNA using real-time PCR," J. Immunol. Methods, 278(1-2):261-9, Jul. 2003.
Yoo et al., "A Comparison of Logistic Regression, Logic Regression, Classification Tree, and Random Forests to Identify Effective Gene-Gene and Gene-Environmental Interactions" International journal of applied science and technology, Aug. 2012, vol. 2, No. 7, pp. 268-284, especially abstract, p. 274, last para, p. 275, 3rd para, last para.
Yuan et al. "The web-based multiplex PCR primer design software Ultiplex and the associated experimental workflow: up to 100-plex multiplicity" BMC Genomics (last accessed Jan. 2021) 22:835 https://doi.org/10.1186/s12864-021-08149-1.
Sominidi-Damodara et al. . "Stromal gene expression predicts sentinel lymph node metastasis of primary cutaneous melanoma (P)" Poster presented at 15th European Association of Dermato-Oncology (EADO) Congress; Apr. 24-27, 2019.
Timar et al. "Gene signature of the metastatic potential of cutaneous melanoma: too much for too little?", Clinical & Experimental Metastasis, Official Journal of Themetastasis Research Society, Kluwer Academic Publishers, DO.vol. 27, No. 6, Feb. 24, 2010 (Feb. 24, 2010), p. 371-387, XP019815757.
Riker et al. "The gene expression profiles of primary and metastatic melanoma yields a transition point of tumor progression and metastasis" BMC Medical Genomics, Apr. 28, 2008, vol. 1, Article No. 13, DOI: 10.1186/1755-8794-1-13.
Singh et al. "CXCL8 and its cognate receptors in melanoma progression and metastasis" Future Oncology, Jan. 2010, vol. 6, No. 1, pp. 111-116, DOI: 10.2217/fon.09.128.
Singh et al. "Expression of interleukin-8 in primary and metastatic malignant melanoma of the skin" Melanoma Research, Aug. 1999, vol. 9, No. 4, pp. 383-387, DOI: 10.1097/00008390-199908000-00007.

* cited by examiner

SEQUENCE LISTING

<160> NUMBER OF SEQ ID NOS: 444

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccaaccgcg agaagatg                                                       18

<210> SEQ ID NO 2
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 2
ggctggggtg ttgaaggt                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcgagaaga tgacccagat                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggtgttga aggtctcaaa                                                20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgacccagat catgtttgag a                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtacatggct ggggtgttg                                                 19

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgaacccca aggccaac                                                  18

<210> SEQ ID NO 8
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
tgatctgggt catcttctcg                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aactctgcat tctcgcttcc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcagacagac actggcaaca                                               20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaccattga aatcctgagt g                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctcccactt tgtctccagt                                               20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcacagagga aactctgcat tc                                            22

<210> SEQ ID NO 14
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 14
ggacaccctc caggaagc                                                        18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atctccaggg gcaccatt                                                        18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agctgcacat cactcaggat t                                                    21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actgctggcc acgagtacg                                                       19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgctccaca ggattcatgg                                                      20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acagagctgt ggttggtgtg                                                      20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 20
ttgtcaattc ggccacct                                                    18

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tatctcctca gccaacagag c                                                21

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agccaccaca ccaaccac                                                    18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgtggccat gaatcctgt                                                   19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccacctccaa aaggatgctc                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctctctttc tggcctggag                                                  20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaatctttgg agtacgctgg a                                    21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggaggctat ccagcgtact                                      20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtgagtaaa cctgaatctt tgg                                  23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccagcgtact ccaaagattc a                                    21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctctgctgg atgacgtgag                                      20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggctatccag cgtactccaa                                      20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 32
gctggatgac gtgagtaaac c                                        21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
accattgagg acctgaggaa                                          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtccactgtg gctgtgagaa                                          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cattgaggac ctgaggaaca                                          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aatctgcaga aggacattgg                                          20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatgacttcc gcaccaagta                                          20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```

```
cgcaggttca actctgtctc                                              20
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
tccgcaccaa gtatgagaca                                              20
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
actcatgcgc aggttcaact                                              20
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
gagcctcgtg actacagcaa                                              20
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
gcaggatgtt ggcattatca gt                                           22
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
aaaaccatcg atgaccttaa aaa                                          23
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gatctgaagc aggatgttgg 20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttcccaagtc aaatgatcca g 21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aagatggttc ccttgttcca 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cggcatttgt tgctcagaat 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gagcctgcat ttcaagttcc 20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttccttcttc accatgcatt t 21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggagccactg ctcaaaaata 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tccaaagatc tgggctatga                                                    20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgaaaagag tctgggtctg aa                                                 22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gagaaaaact gtgaacctgt gg                                                 22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ataagcaggt ggagcattgg                                                    20

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gaagacgaaa tggatacaga gc                                                 22

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtgccaacat gaagactttt atc                                                23

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtggtcagca cccagcttat                                                  20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccaaggcctg cttcttgac                                                   19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gctgtggtcc ttgcatctct                                                  20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcttcataag tctgcgccta                                                  20

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctcctgcaca tgctttgga                                                   19

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aggtctgcgg cagttgtc                                                    18

```
<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aggctttgga agtggtcatt                                                20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccattgtcat ggcaccatct                                                20

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaagtggtca tttcagatgt gatt                                           24

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccattgtcat ggcaccatct                                                20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tggtcatttc agatgtgatt cat                                            23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cattgtcatg gcaccatcta                                                20

<210> SEQ ID NO 69
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtttcgcaga cctgacatcc                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcctcgtctg tagcatcagg                                                  20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cctgacatcc agtaccctga                                                  20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgaggtgatg tcctcgtctg                                                  20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gaatctccta gccccacaga                                                  20

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggtttcttca gaggacacag c                                                21

<210> SEQ ID NO 75
<211> LENGTH: 22
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 75
cccatctcag aagcagaatc tc             22

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
acagcattct gtggggcta             19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ggaaaaccag gacccagag             19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
cttttccccc tttgtcacca             20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
agaaaggtga acccggaaaa             20

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ggtttgcctc tgggtcct             18

<210> SEQ ID NO 81
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 81
gagaaaaggg ccaaaaaggt                                                   20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
catcccctga aatccaggtt                                                   20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aaagggccaa aaaggtgaac                                                   20

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cctggcatcc cctgaaat                                                     18

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtgtcaacct gatggggaga                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gttaacgccc tgactgtggt                                                   20

<210> SEQ ID NO 87
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 87
ggtacagtgg gacagcaggt                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gatctgccat tgtggtaggc                                                   20

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aaccacagtc agggcgtta                                                    19

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gttcgtggcc cttccagt                                                     18

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aagctgaagg tggaggggta                                                   20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gagtcacctg ctgtcccact                                                   20

<210> SEQ ID NO 93
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 93
tattcctccg aaccagcatc                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
caccagctcc gagtcaatgt                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccaccatcaa catggagaac                                               20

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
agtcaatgtc cacagagaac ca                                            22

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
caactgccac attggtgatg                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aaacctcctg ttggcctctt                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
tgacatcacg gatgtgaagc					20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gggttgatga caacctggag					20

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgtgaccgag agcgagaag					19

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
caggctcagt tcaaagtggt t					21

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cggacctttg tcgagtacct					20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gttgctctgc agtgccttct					20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gacttccgtt ggactgatgg          20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tggttgggtc tccaattctc          20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acgtgcaaga aaggaacagt          20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tccaaaggtc ttggcatttt          20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gcagagatgg agcactacgg          20

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cagccttgaa tcctcatgc          19

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggaaggaatc gtggagcag                                              19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cagcagtggg aaccagtaca                                             20

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ctgatgaatg aaatgaggag ga                                          22

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cacaaatgag ccaaatccaa                                             20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagtttgctg tgtgtttgct c                                           21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
catgatttgg catttgcttt t                                           21

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

-continued gccccaccag aggagtatgt                                               20

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aagccgactt ccttcacca                                                19

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gagaccattc ccctcctacc                                               20

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gcttctgtgc catctcaatc t                                             21

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cgaagctgac ctggaagaga                                               20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tgggagtacg gatgcacttt                                               20

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gtgtgcaccg ccaaagat                                                 18

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cgtaccaccg aagatgcag                                                19

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ctaccccggc tactacacca                                               20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gacaaaggcc aggtcaaact                                               20

<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
agtcggggtg gattacgag                                                19

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
acagttgtag cgcaggaacc                                               20

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
atgatgatgg cagggatgg                                                19
```

```
<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcattgatct cggcttcttg                                            20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ctgtggcaca caggaaacac                                            20

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgagggtca tgccacag                                              18

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gccaaagacg ggtttcatta                                            20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gccatgattt tcttcccttc                                            20

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ctcctcctac ggcaaggga                                             19
```

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tggagattgt ctaaccagat ggg                                           23

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctcctacggc aagggagaag                                               20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttgccagtac agtggagatt g                                             21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ccagagctgt gcagatgagt                                               20

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tgcatctaga ttctttgcct ttt                                           23

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
agggcacagc agacttcct                                                19

-continued

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tcgtccatgc tgtggtaatg                                               20

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcatgcacct ctcataccc                                                19

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cgcattgtag gtgtcatagc a                                             21

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cttggcagcc ttcctgatt                                                19

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcaaaactgc accttcacac                                               20

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cgctctgaag gggatctg                                                 18

<210> SEQ ID NO 148

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
acagggtctg ccctctgact                                          20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
gagctcagtc agagggcaga                                          20

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
aactttcccc gttttggtag a                                        21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
tgaacagtgt ggatgagatg g                                        21

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gcagggtgct ttggttgata                                          20

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
aagggtctcc agcacctcta c                                        21

<210> SEQ ID NO 154
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
aaggccttct catggatctt                                                   20

<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gagctccgca aggatgact                                                    19

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
aggacgaggg cgtagaggt                                                    19

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cattcaagga acccagaacc                                                   20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gcgttgaaca aggtttcctc                                                   20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
aagagccaga gtgtcccaag                                                   20

<210> SEQ ID NO 160
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 160
actgagagca ggaccacca                                                   19

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cttctcctgt gtccgctaca a                                                21

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
catggcctga gcacatctc                                                   19

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgcctgcacc tttaagaaag a                                                21

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ccggtcaaac ttcttacact cc                                               22

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165 aaggggaga tgtgctcag                                                    19

<210> SEQ ID NO 166
<211> LENGTH: 18
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 166
cagtccccac agctgcac                                                     18

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aaaccgaagt catagccaca c                                                 21

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
aagctttccg cccattctt                                                    19

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aggcccaaga ctggctacat                                                   20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ctgccatgac ctgttttcct                                                   20

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ggcaggtgcg aaccttatg                                                    19

<210> SEQ ID NO 172
<211> LENGTH: 19
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 172
ccttccagcc aatgttcct                                                    19

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gatcgctgag ctgaaggtg                                                    19

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cggatgcccc atctgagt                                                     18

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
cccattggcg agtttgagaa g                                                 21

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aggaagagtc gaaggtcttg tt                                                22

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ggaagaaact gtggcagagg                                                   20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                       primer

<400> SEQUENCE: 178
ggacaggatt agctcccaca                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acaacgttct gtccccttg                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ggggacagca tcaaatcatc                                              20

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tggatgcaga tgttgttttg a                                            21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cacagctttc catgacgagt t                                            21

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ttgattgaac aaaacagaaa gatca                                        25

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 184
tgacgagtta caagaggagc aa                                             22

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
ctgctcatag cagccacctt                                                20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
aggtgactgg ggcattgatt                                                20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
acgtggagga ggacacagac                                                20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggagccttca gggctacttc                                                20

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agcactgcca aagtggatg                                                 19

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ttgttgacat ggaacaagac c                                          21

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gtgggctaca tcagggtacg                                            20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cagagtcagc caccaactca                                            20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catcatctgg tccaacctca                                            20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gtcctcaggg atggtgtcat                                            20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tgacctcaag atgtgccact                                            20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196

```
tggttggggt caatccagta                                               20
```

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197

```
gatggattcc agttcgagta tg                                            22
```

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198

```
atcaggcgca ggaaggtc                                                 18
```

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199

```
cccaaaaaga gcgtcaggt                                                19
```

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200

```
ttgttgacat ggaacaagac c                                             21
```

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201

```
cttcctaaca gtccgcccta                                               20
```

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
cccgatcagc acagtgattt                                               20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ctgcttcagg gagacacacc                                               20

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tggcttgcaa cttcctcac                                                19

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aggaagttgc aagccaacaa                                               20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
cgaccttccc ttaatcgtct t                                             21

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gcggaggaaa actgtctgg                                                19

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
aaatctgagc agcaccctgt                                               20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
atattcctgg gaatggcaca                                                    20

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ccatactgtg gtaatgttga tga                                                23

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgtcaacaac acagagggag a                                                  21

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
cacgtagttg ctggggatgt                                                    20

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tggcaagatc accagacgg                                                     19

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ggcacctttc gtggtctcac                                                    20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
catgtcgtct tggctcactc                                           20

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
aaattctggc cccaacaata c                                         21

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
catgtcgtct tggctcactc                                           20

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aaattctggc cccaacaata c                                         21

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
aggagccagc gtctaggg                                             18

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ctgcccatca tcatgacct                                            19

```
<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
aacgcaccga atagttacgg                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
catcatcatg acctggatcg                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cactgttacg attcccctga                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
cggctttctc atcaggtttc                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
attagacggc ctcctgcatc                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
agaccagccc ctcttcatct                                              20

<210> SEQ ID NO 227
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ggccccggga attatatct                                                  19

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ccacttcata gtggggttc                                                  20

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ctgcacaact gccacacag                                                  19

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gttctgcatt ggctgggtat                                                 20

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cgtggcaagt gagggttc                                                   19

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
cgaagactcg gaatgagagg g                                               21

<210> SEQ ID NO 233
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gaggcttcct gctctggt                                                       18

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
cgcaaaattg gtgctcagt                                                      19

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gtccgggact tcctaacaga                                                     20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gctgacctcc tggatagtgg                                                     20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gtggtcagca cccagcttat                                                     20

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
ccaaggcctg cttcttgac                                                      19

<210> SEQ ID NO 239
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 239
gctgtggtcc ttgcatctct                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gcttcataag tctgcgccta                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cttccctcag ctttcaggac                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
tctggggtcc tagggaattg                                              20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
acctcaagat gtccctcagc                                              20

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
caggagggtc ctgtacgtg                                               19

<210> SEQ ID NO 245
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 245
gagaccttcg gcgagtacag                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
aaaggccttc tcctcgttgt                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ggcggcaaat actcagtgaa                                              20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
cctgggtgtc ctccttatcc                                              20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
cggatactca cgccagaagt                                              20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
agagatacgc aggtgcaggt                                              20

<210> SEQ ID NO 251
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 251
aagattcgaa caccgacctc                                                    20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gcacttctgg cgtgagtatc                                                    20

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cacgcctgga acaaggac                                                      18

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
atgcacctca tggttgttgg                                                    20

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
caggtgacag gcatcgact                                                     19

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
cgcaggtcac aatacggtta                                                    20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 257
tgaggccctg agagagaaga                                        20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
attccgaaac tccacacgtc                                        20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tcaaggaaat tgagcaacga                                        20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tctgatttgg gcatttgagc                                        20

<210> SEQ ID NO 261
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
tatggtcgac ggtccaaat                                         19

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
tcctcaccac tgatgacagc                                        20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 263
cactgtgacc cacaaaccag                                              20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
gcaagtccaa ctgctatgga                                              20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
tgaggccctg agagagaaga                                              20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
attccgaaac tccacacgtc                                              20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tctactcctt tgggcgagtg                                              20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
cgtccttcag gggaattctt                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 269
taaggacacc ccaaattcca                                                    20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gccaagatga tcagccattc                                                    20

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcagtcaaca gtcgaagaag g                                                  21

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
agctttttct tctgcccaca                                                    20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
agccagcaag cagtgaagtc                                                    20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
tcaggtgact caagcagtgg                                                    20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ccgggagtct atggtcaaac                                              20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
cacggcactc agcttacttg                                              20

<210> SEQ ID NO 277
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
tggagcagtc ttcgtttcg                                               19

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ctggctcctc ttctgaatcg                                              20

<210> SEQ ID NO 279
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gcccgattca gaagaggag                                               19

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
tcatctctgc agatcacttg g                                            21

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
ccagcagagg cataaggttc                                          20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
agtagtgcct tcgggactgg                                          20

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
aggctgattc tggaagttct gagg                                     24

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aatctggact gcttgtggct g                                        21

<210> SEQ ID NO 285
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gttgggcctc caggattta                                           19

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gcctggtagt cctgggaaac                                          20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
tggatggatt gtgttcctga                                          20

```
<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gcctgccttc aagatttctg                                              20

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
ctgagactgt gctgacctgt g                                            21

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctcttcatct ccgccttctg                                              20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
gagaccgcct acatcgaaga                                              20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ggtagcgttc aaacctcctg                                              20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
acaccgtcct caacctgaag                                              20
```

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
aatggccagt gccacatagt                                               20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
ggtgcacttt gtgagcaaga                                               20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
ttggtatgca gatgggttca                                               20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
agctgtggtc caacttctgg                                               20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
gtgtggtaac cgggaaacag                                               20

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
ttcagtttgc tgtgtgtttg c                                             21

```
<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ccaccttctg gagaatccaa                                                      20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
ggcagtattg acagggagga                                                      20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
tactcttgct ggaggctggt                                                      20

<210> SEQ ID NO 303
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gcctattctg tcacttcggc tc                                                   22

<210> SEQ ID NO 304
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
gcaggcacag gtcttgatga ac                                                   22

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gacctctggg aggtgttcag                                                      20

<210> SEQ ID NO 306
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
ttagggatcg acgaaggaga                                                    20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
attcctgcca tcaaccagac                                                    20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
cctgcttctt ggcttcattc                                                    20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
caaagggaca tcccaaaatg                                                    20

<210> SEQ ID NO 310
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
gagtcagcca tgattttctt cc                                                 22

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
taccccgagt acttccagca                                                    20

<210> SEQ ID NO 312
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gatctgcttc caggtcttgc                                                   20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cacacagaca gccactcacc                                                   20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
caggggtggt tattgcatct                                                   20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cagaccccaa ctatgtgcaa                                                   20

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cgcattgtag gtgtcatagc a                                                 21

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
ctctcttggc agccttcct                                                    19

<210> SEQ ID NO 318
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 318
tgaattctca gccctcttca a                                              21

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
tcgccttagt cgtcaccctt                                                20

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
tgtttctcgt caactccacc tcg                                            23

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
ctgatttcat cggggttgtc                                                20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
tgccttgctg aatgaacttg                                                20

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ccagtgaaac agccaccac                                                 19

<210> SEQ ID NO 324
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 324
ctccttccag tgttccaagg                                                   20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ggactctgtc acacccacct                                                   20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
cagggtctca gggaggtctt                                                   20

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tgccagagct gagatgttgt t                                                 21

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
tgtagcattt cggctttcct                                                   20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
ggcaagtact gcgagtgtga                                                   20

<210> SEQ ID NO 330
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 330
attcttttcg gtcgtggatg                                               20

<210> SEQ ID NO 331
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
cactgctgct cctgctcct                                                19

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
tgttcagcat cttttcgatg a                                             21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
tgacaatgac aacatcccag a                                             21

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
tgagtctgcc atgacctgtt                                               20

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
ccctgctcta cacagaacca g                                             21

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 336
acacctggct ccccttttct                                                19

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
gcctggatct tctttctcct ttgc                                           24

<210> SEQ ID NO 338
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
catccagggc gatgtacttg tc                                             22

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339 cccctctga gtcaggaaac                                                 20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
tcatgtgctg tgactgcttg                                                20

<210> SEQ ID NO 341
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
tggacccacc aagattctcc tg                                             22

<210> SEQ ID NO 342
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
gaccacagct ttccatgacg ag                                          22

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
tctgtgcctg ctgctcatag                                             20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
gagtttgggt ttgcttgtcc                                             20

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
cgagaagtgc ccaggaag                                               18

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
agtgagaagc caggaaagca                                             20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tggaaatatc acccacagca                                             20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 348
aggcattttt gcttcacacc                                                20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gctccagctt ctacgtggtc                                                20

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ttaattatcg aagcggtcga a                                              21

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
agccagcaga tcgagaacat                                                20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
ccttcttgag gttgccagtc                                                20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
caccaatcac cccattaacc                                                20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
```
gcttgagctg agctttttcc                                              20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
ccaggtgctg gaaaaagaag                                              20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
gagctgctct gcctgagtct                                              20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
gcagacacac ctgttggaaa                                              20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gaacgacctt cccttaatcg                                              20

<210> SEQ ID NO 359
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
cctactacat ccaggcgtcc ac                                           22

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360

```
atgcaaatcg cctgtggtag c                                          21

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
ctgttcggag gcttcaactc                                            20

<210> SEQ ID NO 362
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
agggatctcc caggcatc                                              18

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
tacctgggat cacctccatc                                            20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
acagggatcc tcagtgtcgt                                            20

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
cgggatgagt tgggaggag                                             19

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ttagggcttc ctcttggaga                                            20
```

<210> SEQ ID NO 367
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
atggtgcgca ggttcttg                                          18

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
accagcgtgt ccaggaag                                          18

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
gagcagcatg gagccttc                                          18

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
gcatggttac tgcctctggt                                        20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
caaacagaca aggctggtga                                        20

<210> SEQ ID NO 372
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
tcaatctcat ctggattttt gg                                     22

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
ctgcaggtgg acaacagaaa                                               20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
catcagccag aatcccatct                                               20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
gtccccagag agacctgttt                                               20

<210> SEQ ID NO 376
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
agacacaatt ggcgcaggt                                                19

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
aagactggac gcgatagctg                                               20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
ggttgttcct gagacgctgt                                               20

-continued

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 379
tacaccagac ccgtgttcct                                               20

<210> SEQ ID NO 380
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 380
tccaggtcaa acttctcgaa gg                                            22

<210> SEQ ID NO 381
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 381
cttcaatgcc cagctcca                                                 18

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 382
ttcccaacca catcttccac                                               20

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 383
ctgctgctct tgggcact                                                 18

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 384
cagcagtcaa agggatgac                                                20

<210> SEQ ID NO 385

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
aggattccta tgtgggcgac g                                          21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
tcaggcagct cgtagctctt c                                          21

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
ggaatgtggg ctttgtgttc acc                                        23

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
aggccaggac tcgtttgtac c                                          21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
acatcaaggg catcgtcaag g                                          21

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
tctctttctc ctgcacagtc ttgg                                       24

<210> SEQ ID NO 391
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
tgctcgcgct actctctctt tc                                            22

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tcacatggtt cacacggcag                                               20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
tggccttctc tctggaaatg                                               20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
tcatttcctc ctcgtggttc                                               20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
aggtgaccat gcagaacctc                                               20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
cctcgtggtt cttcttcagg                                               20

<210> SEQ ID NO 397
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 397
gaaatcttgg gcttgatgga                                              20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
ccgaggttgt tgttgaaggt                                              20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
ccatggataa agctgccaat                                              20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
gacacagcaa gctcacaagc                                              20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
cactcttaca ccacggctga                                              20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
cataagcagg tggagcattg                                              20

<210> SEQ ID NO 403
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 403
ttgtccaggg tattgaaagt gc                                              22

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
gacaagagca gaagatgcgg g                                               21

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
gcgttggaac agaggttgga g                                               21

<210> SEQ ID NO 406
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
caggtgtctc aagggtagca gg                                              22

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
cttccctttc gccacagtat g                                               21

<210> SEQ ID NO 408
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
cctccttctc cttcttgcca ct                                              22

<210> SEQ ID NO 409
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 409
aatggctctc agatgctcct gg                                              22

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
gattctgcca gcagttggtc c                                               21

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
accacagctt cctggtggag                                                 20

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
gagcggatgg gcttcttgat g                                               21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
aacgtgacct tgtctcccaa c                                               21

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
gcatgacatc gccgattctt                                                 20

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 415
ttcaacaagc ccacccacta c                                              21

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
gttctcaatg acagggatgc g                                              21

<210> SEQ ID NO 417
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
catggaatac ctggagggca ac                                             22

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
caggtgccag cagttcttca t                                              21

<210> SEQ ID NO 419
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
tctcagagct tctctacatc ac                                             22

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
ctgacgactc cttgttcacc a                                              21

<210> SEQ ID NO 421
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
tcacctcctc tgtaccattg c					21

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ctcatctcca atgccctcga					20

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
tgcaatgaag agagggctct g					21

<210> SEQ ID NO 424
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
cgtggccctg gtatctattt ca				22

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
ggctacagct tcaccaccac					20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
taatgtcacg cacgatttcc					20

<210> SEQ ID NO 427
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 427
cccagccagg aaatccat                                                    18

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
ctggctcctc ttctgaatcg                                                  20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
cagtgcctgt caaaagttgc                                                  20

<210> SEQ ID NO 430
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
ccccgttgaa acaccttg                                                    18

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
gaccttggaa acccaatgaa                                                  20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
tccatctctg actgctggtg                                                  20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
```
tgctatccct gtacgcctct                                                20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
gagtccatca cgatgccagt                                                20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
ggacttcgag caagagatgg                                                20

<210> SEQ ID NO 436
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
cttctccagg gaggagctg                                                 19

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
gatgcagatt gagagcctga                                                20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
ttcttcaggt aggccagctc                                                20

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439

```
ggtggtatgt gaccttggaa a                                              21

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
gcacactgaa acgaagacca                                                20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gaaggatttg ctgggaagtg                                                20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
cgtggccctg gtatctattt                                                20

<210> SEQ ID NO 443
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
tacttggaaa atcacagttc ccg                                            23

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
tgaatcggaa attgagaacg act                                            23
```

METHODS AND MATERIALS FOR IDENTIFYING MALIGNANT SKIN LESIONS

CROSS-REFERENCE TO RELATED APPLICATIONS

This application is a continuation of co-pending U.S. patent application Ser. No. 14/442,673, filed May 13, 2015, now abandoned, which is a National Stage application under 35 U.S.C. § 371 of International Patent Application PCT/US2013/053982, having an International filing date of Aug. 7, 2013, designating the United States of America and published in English as International Patent Publication WO 2014/077915 A1 on May 22, 2014, which claims the benefit under Article 8 of the Patent Cooperation Treaty to U.S. Provisional Patent Application Ser. No. 61/726,217, filed Nov. 14, 2012, the disclosure of each of which is hereby incorporated herein in its entirety by this reference.

STATEMENT ACCORDING TO 37 C.F.R. § 1.821(c) or (e)—REQUEST TO TRANSFER COMPUTER-READABLE FORM OF SEQUENCE LISTING FROM PARENT APPLICATION

Pursuant to 37 C.F.R. § 1.821(c) or (e), the transmittal documents of this application include a Request to Transfer Computer-Readable Form of the Sequence Listing from the parent application, the contents of the Sequence Listing are incorporated herein by this reference.

TECHNICAL FIELD

This document relates to methods and materials for identifying malignant skin lesions (e.g., malignant pigmented skin lesions). For example, this document relates to methods and materials for using quantitative PCR results and correction protocols to reduce the impact of basal keratinocyte contamination on the analysis of test sample results to identify malignant skin lesions.

BACKGROUND

Malignant skin lesions are typically identified by obtaining a skin biopsy and morphologically assessing the biopsy's melanocytes under a microscope. Such a procedure can be difficult to standardize and can lead to overcalling of melanomas.

Once a diagnosis of melanoma is made by morphological assessment, the risk of metastasis is typically determined by the invasion depth of malignant cells into the skin (i.e., the Breslow depth). The Breslow depth can dictate further work-up such as a need for an invasive sentinel lymph node (SLN) procedure. Such procedures, however, can lead to inaccurate determinations of the true malignant potential of a pigmented lesion.

BRIEF SUMMARY

Provided are methods and materials for identifying malignant skin lesions (e.g., malignant pigmented skin lesions). For example, this document provides methods and materials for using quantitative PCR results and correction protocols to reduce the impact of basal keratinocyte contamination on the analysis of test sample results to identify malignant skin lesions.

As described herein, quantitative PCR can be performed using a routine skin biopsy sample (e.g., a paraffin-embedded tissue biopsy) to obtain expression data (e.g., gene copy numbers) for one or more marker genes. Correction protocols can be used to reduce the impact of basal keratinocyte contamination on the analysis of the expression data from the test sample. For example, the contribution of gene expression from basal keratinocytes present within the test skin sample can be determined and removed from the overall gene expression values to determine the final gene expression value for a particular gene as expressed from cells other than basal keratinocytes (e.g., melanocytes). An assessment of the final gene expression values, which include minimal, if any, contribution from basal keratinocytes, for a collection of marker genes can be used to determine the benign or malignant biological behavior of the tested skin lesion.

In general, one aspect hereof features a method for identifying a malignant skin lesion. The method comprises, or consists essentially of, (a) determining, within a test sample, the expression level of a marker gene selected from the group consisting of PLAT, SPP1, TNC, ITGB3, COL4A1, CD44, CSK, THBS1, CTGF, VCAN, FARP1, GDF15, ITGB1, PTK2, PLOD3, ITGA3, IL8, and CXCL1 to obtain a measured expression level of the marker gene for the test sample, (b) determining, within the test sample, the expression level of a keratinocyte marker gene to obtain a measured expression level of the keratinocyte marker gene for the test sample, (c) removing, from the measured expression level of the marker gene for the test sample, a level of expression attributable to keratinocytes present in the test sample using the measured expression level of the keratinocyte marker gene for the test sample and a keratinocyte correction factor to obtain a corrected value of marker gene expression for the test sample, and (d) identifying the test sample as containing a malignant skin lesion based, at least in part, on the corrected value of marker gene expression for the test sample. The keratinocyte marker gene can be K14. The marker gene can be SPP1. The step (c) can comprise (i) multiplying the measured expression level of the keratinocyte marker gene for the test sample by the keratinocyte correction factor to obtain a correction value and (ii) subtracting the correction value from the measured expression level of the marker gene for the test sample to obtain the corrected value of marker gene expression for the test sample.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION

This document provides methods and materials for identifying malignant skin lesions (e.g., malignant pigmented skin lesions). For example, this document provides methods and materials for using quantitative PCR results and correction protocols to reduce the impact of basal keratinocyte contamination on the analysis of test sample results to identify malignant skin lesions.

Figure 1:
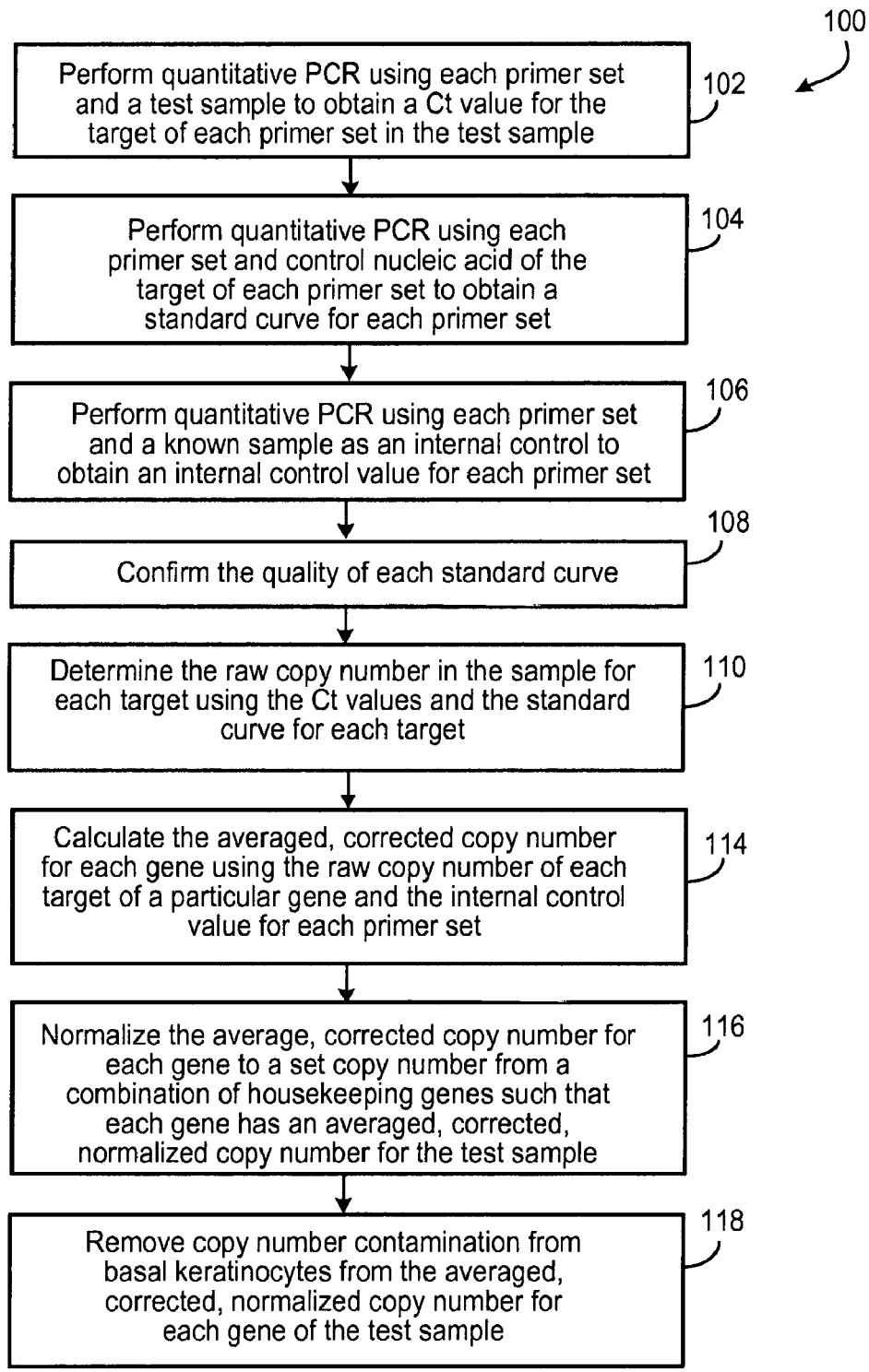
FIG. 1 is a flow chart of an exemplary process for determining the gene expression value, which includes minimal, if any, contribution from basal keratinocytes, for a marker gene by cells within a tested sample (e.g., a tested skin biopsy sample).

FIG. 1 shows an exemplary process 100 for determining a gene expression value, which includes minimal, if any, contribution from basal keratinocytes, for a marker gene by cells within a tested sample (e.g., a tested skin biopsy sample). The process begins at box 102, where quantitative PCR using a collection of primer sets and a test sample is used to obtain a Ct value for the target of each primer set. Each gene of interest can be assessed using a single primer set or multiple different primer sets (e.g., two, three, four, five, six, seven, or more different primer sets). In some cases, quantitative PCR is performed using each primer set and control nucleic acid of the target of each primer set (e.g., linearized cDNA fragments) to obtain a standard curve for each primer set as set forth in box 104. In some cases, quantitative PCR is performed using each primer set and a known sample as an internal control (e.g., a stock biological sample) to obtain an internal control value for each primer set as set forth in box 106. This internal control can be used to set values for each primer set across different assays. In some cases, the quantitative PCR performed according to boxes 102, 104, and 106 can be performed in parallel. For example, the quantitative PCR performed according to boxes 102, 104, and 106 can be performed in a single 96 well format.

At box 108, the quality of the obtained standard curves can be confirmed. In some cases, a gene of interest included in the assay format can be a melanocyte marker (e.g., levels of MLANA and/or MITF expression) to confirm the presence of melanocytes in the test sample. Other examples of melanocyte markers that can be used as described herein include, without limitation, TYR, TYRP1, DCT, PMEL, OCA2, MLPH, and MC1R.

At box 110, the raw copy number of each target present in the test sample is determined using the Ct values and the standard curve for each target. In some cases, the averaged, corrected copy number for each gene is calculated using the raw copy number of each target of a particular gene and the internal control value for each primer set (box 112). This averaged, corrected copy number value for each gene can be normalized to a set number of one or more housekeeping genes as set forth in box 114. For example, each averaged, corrected copy number value for each gene can be normalized to 100,000 copies of the combination of ACTB, RPL8, RPLP0, and B2M. Other examples of housekeeping genes that can be used as described herein include, without limitation, RRN18S, GAPD, PGK1, PPIA, RPL13A, YWHAZ, SDHA, TFRC, ALAS1, GUSB, HMBS, HPRT1, TBP, and TUPP. Once normalized, the copy number values for each gene can be referred to as the averaged, corrected, normalized copy number for that gene as present in the test sample.

At box 116, the averaged, corrected, normalized copy number for each gene can be adjusted to remove the copy number contamination from basal keratinocytes present in the test sample. In general, copy number contamination from basal keratinocytes can be removed by (a) determining a keratinocyte correction factor for the gene of interest using one or more keratinocyte markers (e.g., keratin 14 (K14)) and one or more normal skin samples (e.g., FFPE-embedded normal skin samples), (b) determining the averaged, corrected, normalized copy number value for the one or more keratinocyte markers of the test sample and multiplying that value by the keratinocyte correction factor to obtain a correction value for the gene of interest, and (c) subtracting that correction value from the averaged, corrected, normalized copy number value of the gene of interest to obtain the final copy number for the gene of interest. Examples of keratinocyte markers that can be used as described herein include, without limitation, KRT5, KRT1, KRT10, KRT17, ITGB4, ITGA6, PLEC, DST, and COL17A1.

Figure 2:
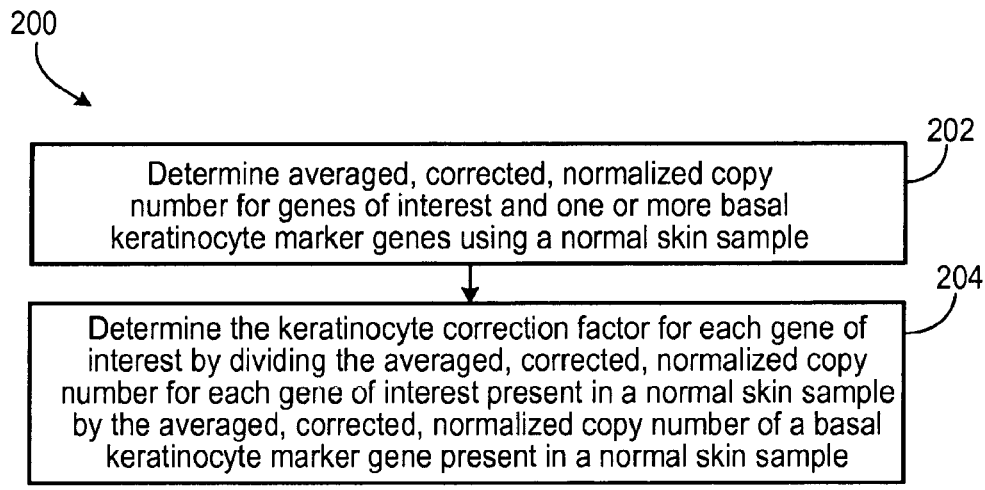
FIG. 2 is a flow chart of an exemplary process for determining a keratinocyte correction factor for a marker gene of interest.

With reference to FIG. 2, process 200 can be used to obtain a keratinocyte correction factor for a gene of interest. At box 202, the averaged, corrected, normalized copy number for one or more genes of interest (e.g., Gene X) and one or more basal keratinocyte marker genes (e.g., K14) are determined using one or more normal skin samples and procedures similar to those described in FIG. 1. As box 204, the keratinocyte correction factor for each gene of interest (e.g., Gene X) is determined by dividing the averaged, corrected, normalized copy number for each gene of interest present in a normal skin sample by the averaged, corrected, normalized copy number of a basal keratinocyte marker gene present in a normal skin sample. Examples of keratinocyte correction factors for particular genes of interest are set forth in Table E under column "AVG per copy K14."

Figure 3:
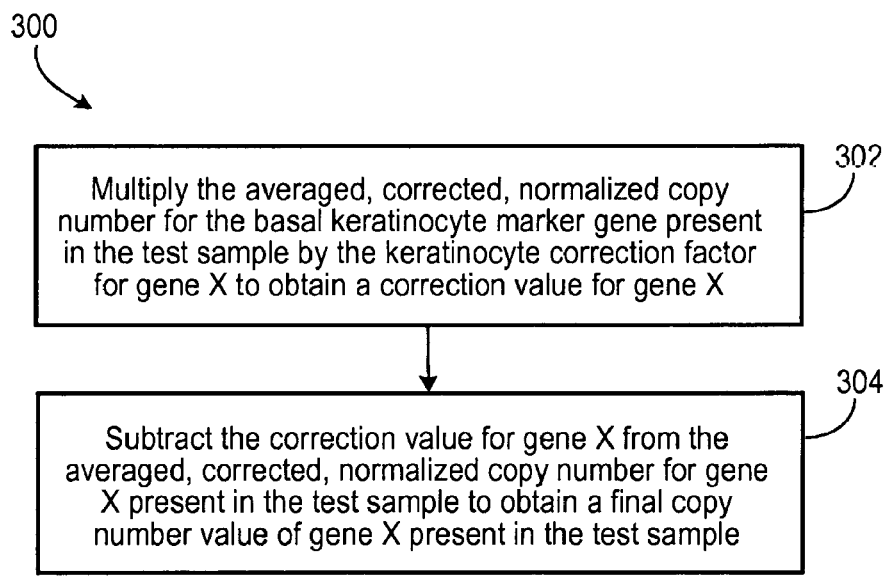
FIG. 3 is a flow chart of an exemplary process for removing copy number contamination from basal keratinocytes from a copy number value for a marker gene to determine the gene expression value, which includes minimal, if any, contribution from basal keratinocytes, for that marker gene by cells within a tested sample (e.g., a tested skin biopsy sample).

With reference to FIG. 3, once a keratinocyte correction factor in determined for a particular gene of interest (e.g., Gene X), then the averaged, corrected, normalized copy number for the basal keratinocyte marker gene present in the test sample can be multiplied by the keratinocyte correction factor for the gene of interest (e.g., Gene X) to obtain a correction value for the gene of interest (e.g., Gene X). See, e.g., box 302. At box 304, the correction value for the gene of interest (e.g., Gene X) is subtracted from the averaged, corrected, normalized copy number for the gene of interest (e.g., Gene X) present in the test sample to obtain a final copy number value of the gene of interest (e.g., Gene X) present in the test sample.

Figure 4:
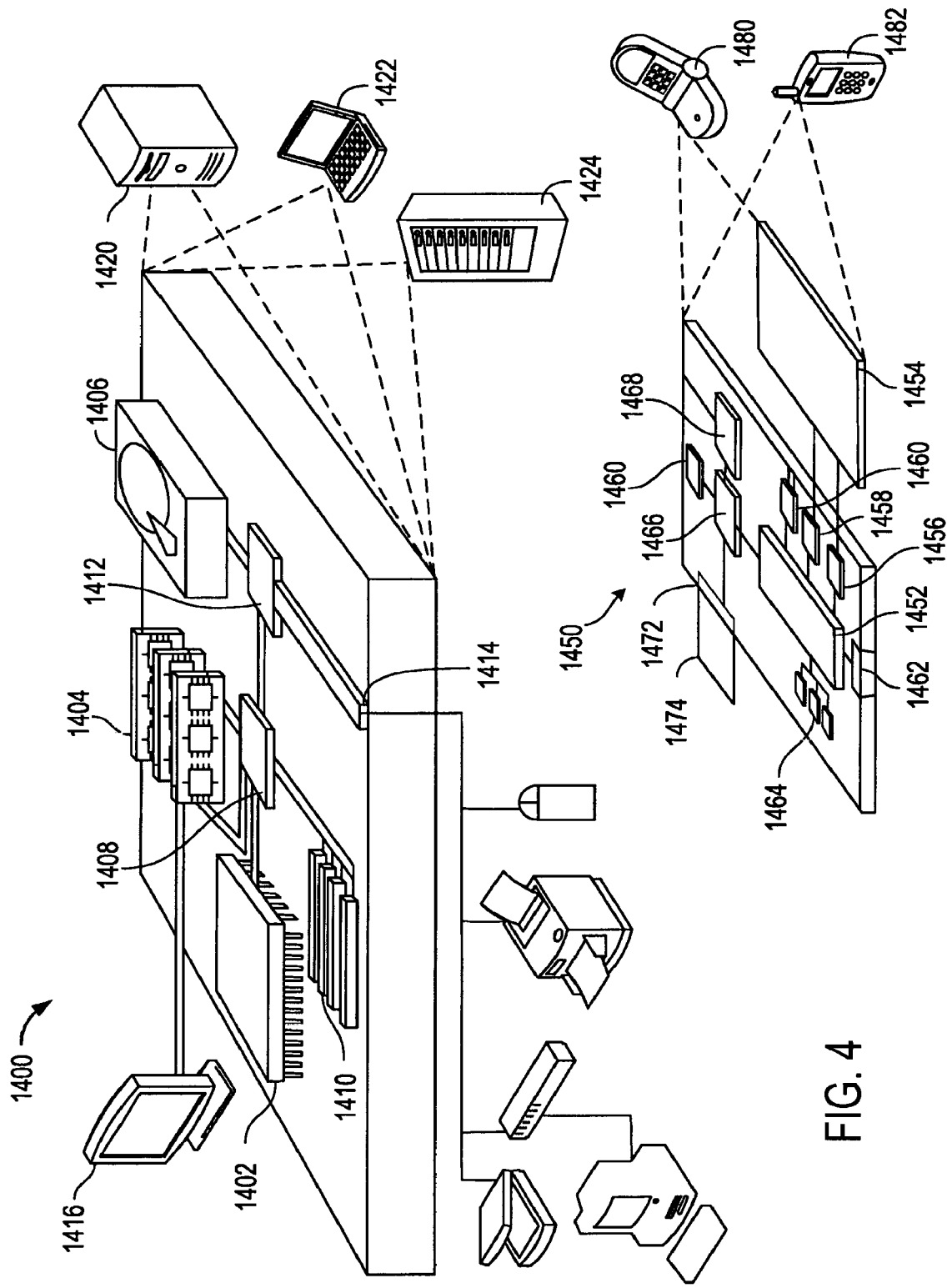
FIG. 4 is a diagram of an example of a generic computer device and a generic mobile computer device that can be used as described herein.

FIG. 4 is a diagram of an example of a generic computer device 1400 and a generic mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in FIG. 4. For example, it may be implemented as a standard server 1420, or multiple times in a group of such servers. It may also be implemented as part of a rack server system 1424. In addition, it may be implemented in a personal computer such as a laptop computer 1422. In some cases, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in FIG. 4. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network).

Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

The invention will be further described in the following examples, which do not limit the scope of the invention described in the claims.

EXAMPLES

Example 1—Marker Genes that Discriminate Between Benign and Malignant Tissue

Marker genes were ordered by their ability to differentiate benign from malignant tissue (Table A). This was based on the analysis of 73 benign and 53 malignant tissues, and the hypothesis that changes in expression of fibronectin-associated gene networks are indicative of malignant cell behavior. Values of the test statistic were for the Wilcoxon rank sum test. The values of the test statistic for a Winsorized two-sample test (trimmed outliers were replaced with actual values) and for the chi-square test for the zero vs. >zero versions of each variable were included. The top 5 discriminatory genes based on each statistical test were highlighted in bold.

TABLE A

| gene | Test statistic value | | |
|---|---|---|---|
| | Wilcoxon rank sum test | Winsorized two-sample t-test | Chi- square test |
| FN1 | −10.2312 | −8.04081 | 106.714 |
| SPP1 | −9.0279 | −4.9374 | 86.774 |

TABLE A-continued

| gene | Wilcoxon rank sum test | Winsorized two-sample t-test | Chi- square test |
|---|---|---|---|
| COL4A1 | −8.8807 | −7.27171 | 83.711 |
| TNC | −8.7511 | −8.31049 | 75.549 |
| ITGA3 | −8.6008 | −5.86334 | 79.788 |
| LOXL3 | −8.1978 | −6.75327 | 75.144 |
| AGRN | −8.1243 | −7.91238 | 62.611 |
| VCAN | −8.0812 | −6.24088 | 67.388 |
| PLOD3 | −8.0384 | −6.89248 | 62.691 |
| ITGB1 | −8.0021 | −7.38143 | 59.973 |
| PTK2 | −7.5279 | −7.19889 | 54.446 |
| CTGF | −7.4997 | −5.581 | 57.79 |
| PLOD1 | −7.332 | −7.36126 | 44.87 |
| LAMC1 | −7.2425 | −6.1057 | 54.233 |
| THBS1 | −7.2425 | −5.60331 | 54.233 |
| LOXL2 | −7.2241 | −6.33208 | 55.909 |
| IL6 | −7.1777 | −6.41883 | 56.966 |
| LOXL1 | −7.1279 | −6.34431 | 52.878 |
| IL8 | −7.1194 | −5.76042 | 57.296 |
| CYR61 | −6.741 | −6.97388 | 43.866 |
| ITGAV | −6.5947 | −6.27571 | 47.021 |
| YAP | −6.4848 | −6.36431 | 42.417 |
| BGN | −6.3419 | −6.01066 | 25.387 |
| LAMB1 | −6.3293 | −5.68826 | 37.061 |
| ITGB3 | −6.3142 | −5.13158 | 40.835 |
| CXCL1 | −6.1077 | −5.66564 | 40.137 |
| THBS2 | −6.0427 | −5.02003 | 37.413 |
| COL18A1 | −6.0379 | −4.9125 | 41.339 |
| SPARC | −6.0272 | −6.39324 | 38.098 |
| TP53 | −6.0182 | −6.18554 | 34.945 |
| PLOD2 | −5.9082 | −3.50272 | 47.576 |
| CCL2 | −5.8844 | −5.38758 | 30.69 |
| FBLN2 | −5.5848 | −4.59826 | 31.913 |
| LAMA1 | −5.4876 | −4.2817 | 31.071 |
| THBS4 | −5.3971 | −3.88786 | 35.27 |
| COL1A1 | −5.325 | −4.37617 | 34.693 |
| ITGA5 | −4.9847 | −3.56695 | 25.243 |
| TAZ | −4.036 | −3.26011 | 18.313 |
| POSTN | −3.8054 | −2.78378 | 19.813 |
| LOX | −3.728 | −2.8677 | 17.157 |
| CSRC | −3.7078 | −3.71759 | 13.983 |
| LAMA3 | −3.5805 | −2.99652 | 13.391 |
| CDKN1A | −3.5766 | −3.20447 | 17.228 |
| CDKN2A | −3.5491 | −2.90903 | 15.938 |
| ITGA2 | −3.4083 | −2.72495 | 11.766 |
| LAMC2 | −3.4083 | −2.53784 | 11.766 |
| PCOLCE2 | −3.3469 | −3.53676 | 14.449 |
| LOXL4 | −3.2079 | −2.76128 | 10.943 |
| PCOLCE | −2.2172 | −1.13805 | 7.993 |
| LAMB3 | −1.2822 | 0.89459 | 7.028 |
| CSF2 | 2.175 | 1.93095 | 4.522 |

Example 2—Marker Panel Revision after Statistical Analysis

The candidate gene list from Example 1 was modified to include other FN1 network genes as well as four housekeeping genes (ACTB, RPLP0, RPL8, and B2M), two keratinocyte markers (K10 and K14) to assess keratinocyte contamination, and four melanocyte markers (MITF, TYR, MLANA and PMEL) to assess melanocyte content in the skin sections. Genes from Example 1 with low discriminatory value and a more distant neighborhood to FN1 were excluded from the test setup (LAMC1, LOXL2, CYR61, YAP, BGN, LAMB1, THBS2, COL18A1, SPARC, TP53, PLOD2, CCL2, FBLN2, LAMA1, THBS4, COL1A1, TAZ, POSTN, LOX, CSRC, LAMA3, CDKN1A, CDKN2A, LAMC2, PCOLCE2, LOXL4, PCOLCE, LAMB3, and CSF2). Instead, the discriminatory ability of other FN1 network genes was determined (PLAT, CSK, GDF15, FARP1, ARPC1B, NES, NTRK3, SNX17, L1CAM, and CD44). The following results were based on the analysis of 26 benign nevi and 52 primary cutaneous melanomas with documented subsequent metastasis or skin lesions of melanoma metastasis (Table B). The top 5 genes were highlighted.

TABLE B

| gene | Wilcoxon rank sum test | Winsorized two-sample t-test | Chi-square test |
|---|---|---|---|
| COL4A1 | −5.85975 | −5.42545 | 46.3273 |
| FN1 | −5.50862 | −3.63639 | 35.1951 |
| PLAT | −4.82670 | −3.13568 | 25.7234 |
| IL8 | −4.61443 | −4.41668 | 28.6000 |
| SPP1 | −4.60153 | −3.08137 | 23.0816 |
| PLOD3 | −4.37001 | −3.91553 | 18.8036 |
| TNC | −4.26431 | −3.14128 | 19.5000 |
| CXCL1 | −4.24452 | −3.76681 | 20.6471 |
| CSK | −4.15178 | −2.96444 | 18.3962 |
| GDF15 | −4.01364 | −2.99752 | 13.7083 |
| ITGB3 | −3.92608 | −2.80068 | 16.3091 |
| CCL2 | −3.61870 | −3.45423 | 17.5176 |
| VCAN | −3.46906 | −2.26781 | 12.5593 |
| ITGB1 | −3.40897 | −3.63399 | 5.0221 |
| PLOD1 | −3.40380 | −3.20309 | 9.2625 |
| CTGF | −3.11725 | −2.20507 | 10.0645 |
| THBS1 | −3.11721 | −2.01257 | 10.0645 |
| ITGA3 | −3.04915 | −2.65398 | 7.5341 |
| FARP1 | −2.99724 | −2.28024 | 9.2857 |
| AGRN | −2.92104 | −3.30679 | 1.8838 |
| IL6 | −2.85960 | −3.05600 | 10.6257 |
| LOXL3 | −2.84999 | −2.70498 | 5.1096 |
| LOXL1 | −2.69957 | −2.11477 | 8.1250 |
| ARPC1B | −2.57571 | −2.82320 | All but 1 value > 0 |
| NES | −2.45264 | −2.70056 | 2.4375 |
| PTK2 | −2.22328 | −2.26180 | 4.4057 |
| ITGA2 | −2.08353 | −1.50078 | 4.4571 |
| ITGA5 | −1.93478 | −1.39663 | 3.8451 |
| ITGAV | −1.29341 | −0.81964 | 3.5615 |
| NTRK3 | −1.22485 | 75 of the 78 values are = 0 | |
| MITF | 0.58305 | 0.73916 | 0.4274 |
| SNX17 | 0.74754 | 0.90733 | 0.0785 |
| L1CAM | 1.61125 | 0.27151 | 2.1081 |
| MLANA | 2.96258 | 2.92548 | All values > 0 |
| CD44 | 5.23089 | 7.17590 | All but 1 value > 0 |

Figure 7:
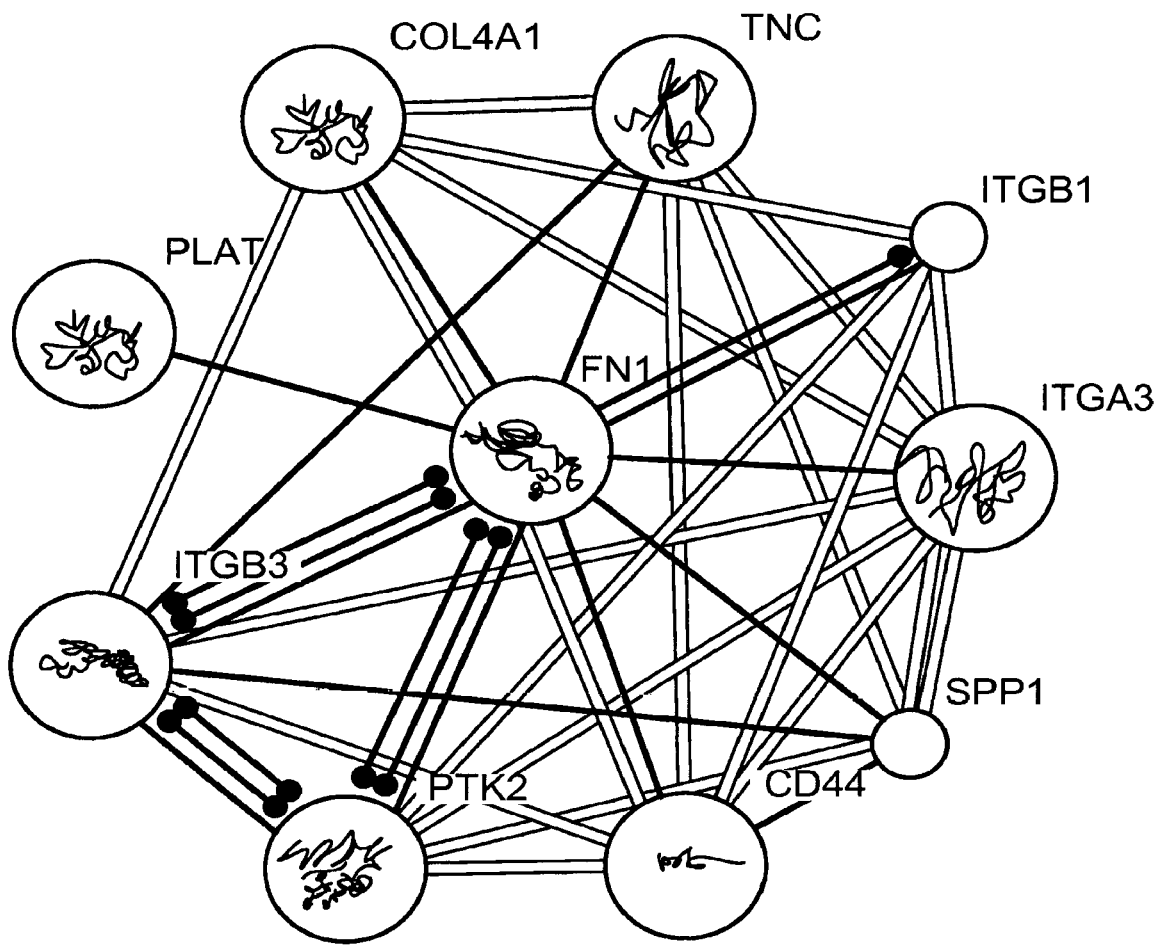
FIG. 7 is a network diagram.

Based on the results of Example 1 and above, FN1 was identified as a component of the melanoma phenotype that is at the core of a gene network that discriminates between benign and malignant melanocytic skin lesions (FIG. 7). The modeling was based on the STRING 9.0 database (string-db.org).

The list of all 71 genes tested is provided in Table 1.

TABLE 1

List of genes used to discriminate benign skin tissue lesions from malignant skin tissue lesions.

| Gene Name | GenBank ® Accession No. | GenBank ® GI No. |
|---|---|---|
| FN1 | NM_212482 | 47132556 |
| | NM_002026 | 47132558 |
| | NM_212474 | 47132548 |
| | NM_212476 | 47132552 |
| | NM_212478 | 47132554 |
| | NM_054034 | 47132546 |
| SPP1 | NM_001040058 | 91206461 |
| | NM_001040060 | 91598938 |
| | NM_000582 | 38146097 |
| COL4A1 | NM_001845 | 148536824 |
| TNC | NM_002160 | 340745336 |
| ITGA3 | NM_005501 | 171846264 |
| | NM_002204 | 171846266 |

TABLE 1-continued

List of genes used to discriminate benign skin tissue lesions from malignant skin tissue lesions.

| Gene Name | GenBank® Accession No. | GenBank® GI No. |
|---|---|---|
| LOXL3 | NM_032603 | 22095373 |
| AGRN | NM_198576 | 344179122 |
| VCAN | NM_004385 | 255918074 |
|  | NM_001164098 | 255918078 |
|  | NM_001164097 | 255918076 |
| PLOD3 | NM_001084 | 62739167 |
| ITGB1 | NM_002211 | 182519230 |
|  | NM_133376 | 182507162 |
|  | NM_033668 | 182507160 |
| PTK2 | NM_001199649 | 313851043 |
|  | NM_005607 | 313851042 |
|  | NM_153831 | 313851041 |
| CTGF | NM_001901 | 98986335 |
| PLOD1 | NM_000302 | 324710986 |
| LAMC1 | NM_002293 | 145309325 |
| THBS1 | NM_003246 | 40317625 |
| LOXL2 | NM_002318 | 67782347 |
| IL6 | NM_000600 | 224831235 |
| LOXL1 | NM_005576 | 67782345 |
| IL8 | NM_000584 | 324073503 |
| CYR61 | NM_001554 | 197313774 |
| ITGAV | NM_001144999 | 223468594 |
|  | NM_001145000 | 223468596 |
|  | NM_002210 | 223468593 |
| YAP | NM_001130145 | 303523503 |
|  | NM_001195045 | 303523626 |
|  | NM_006106 | 303523510 |
|  | NM_001195044 | 303523609 |
| BGN | NM_001711 | 268607602 |
| LAMB1 | NM_002291 | 167614503 |
| ITGB3 | NM_000212 | 47078291 |
| CXCL1 | NM_001511 | 373432598 |
| THBS2 | NM_003247 | 40317627 |
| COL18A1 | NM_030582 | 110611234 |
|  | NM_130445 | 110611232 |
| SPARC | NM_003118 | 365777426 |
| TP53 | NM_000546 | 371502114 |
|  | NM_001126112 | 371502115 |
|  | NM_001126114 | 371502117 |
|  | NM_001126113 | 371502116 |
| PLOD2 | NM_182943 | 62739164 |
|  | NM_000935 | 62739165 |
| CCL2 | NM_002982 | 56119169 |
| FBLN2 | NM_001998 | 51873054 |
|  | NM_001004019 | 51873052 |
|  | NM_001165035 | 259013546 |
| LAMA1 | NM_005559 | 329112585 |
| THBS4 | NM_003248 | 291167798 |
| COL1A1 | NM_000088 | 110349771 |
| ITGA5 | NM_002205 | 56237028 |
| TAZ | NM_000116 | 195232764 |
|  | NM_181311 | 195232766 |
|  | NM_181312 | 195232765 |
|  | NM_181313 | 195232767 |
| POSTN | NM_001135934 | 209862910 |
|  | NM_006475 | 209862906 |
|  | NM_001135935 | 209863010 |
| LOX | NM_001178102 | 296010939 |
|  | NM_002317 | 296010938 |
| CSRC | NM_005417 | 38202215 |
|  | NM_198291 | 38202216 |
| LAMA3 | NM_198129 | 38045909 |
|  | NM_001127717 | 189217424 |
| CDKN1A | NM_000389 | 310832422 |
|  | NM_001220777 | 334085239 |
|  | NM_078467 | 310832423 |
|  | NM_001220778 | 334085241 |
| CDKN2A | NM_000077 | 300863097 |
|  | NM_058195 | 300863095 |
|  | NM_001195132 | 304376271 |
| ITGA2 | NM_002203 | 116295257 |
| LAMC2 | NM_005562 | 157419137 |
|  | NM_018891 | 157419139 |
| PCOLCE2 | NM_013363 | 296317252 |
| LOXL4 | NM_032211 | 67782348 |

TABLE 1-continued

List of genes used to discriminate benign skin tissue lesions from malignant skin tissue lesions.

| Gene Name | GenBank® Accession No. | GenBank® GI No. |
|---|---|---|
| PCOLCE | NM_002593 | 157653328 |
| LAMB3 | NM_000228 | 62868214 |
|  | NM_001017402 | 62868216 |
|  | NM_001127641 | 189083718 |
| CSF2 | NM_000758 | 371502128 |
| ACTB | NM_001101 | 168480144 |
| RPLP0 | NM_053275 | 49087137 |
|  | NM_001002 | 49087144 |
| RPL8 | NM_000973 | 72377361 |
|  | NM_033301 | 15431305 |
| B2M | NM_004048 | 37704380 |
| K10 | NM_000421 | 195972865 |
| K14 | NM_000526 | 197313720 |
| MITF | NM_198158 | 296841082 |
|  | NM_198177 | 296841080 |
|  | NM_006722 | 296841079 |
|  | NM_198159 | 296841078 |
|  | NM_000248 | 296841081 |
|  | NM_001184967 | 296841084 |
|  | NM_198178 | 296923803 |
| TYR | NM_000372 | 113722118 |
| MLANA | NM_005511 | 5031912 |
| PMEL | NM_001200054 | 318037594 |
|  | NM_001200053 | 318037592 |
|  | NM_006928 | 318068057 |
| NES | NM_006617 | 38176299 |
| L1CAM | NM_024003 | 221316758 |
|  | NM_001143963 | 221316759 |
|  | NM_000425 | 221316755 |
| GDF15 | NM_004864 | 153792494 |
| ARPC1B | NM_005720 | 325197176 |
| FARP1 | NM_005766 | 48928036 |
|  | NM_001001715 | 159032536 |
| NTRK3 | NM_001007156 | 340745351 |
|  | NM_001012338 | 340745349 |
|  | NM_001243101 | 340745352 |
|  | NM_002530 | 340745350 |
| CSK | NM_001127190 | 187475372 |
|  | NM_004383 | 187475371 |
| CD44 | NM_001001391 | 48255940 |
|  | NM_001001392 | 48255942 |
|  | NM_001202556 | 321400139 |
|  | NM_001001389 | 48255936 |
|  | NM_000610 | 48255934 |
|  | NM_001001390 | 48255938 |
|  | NM_001202555 | 321400137 |
|  | NM_001202557 | 321400141 |
| SNX17 | NM_014748 | 388596703 |
| PLAT | NM_000930 | 132626665 |
|  | NM_033011 | 132626641 |

Gene expression of target genes was assessed by SYBR/EVA-Green based RT-PCR. All tested genes were accompanied by a standard curve for quantification of absolute copy number per a defined number of housekeeping genes. mRNA extraction from paraffin-embedded biospecimen was performed using an extraction protocol (Qiagen RNA FFPE extraction kit) and an extraction robot (Qiacube from Qiagen). mRNA was transcribed into cDNA using a commercially available kit (iScript kit from BioRad), and Fluidigm technology was used for PCR cycling.

The primer design was performed using web-based open access software. The primers were HPLC purified to minimize background and were optimized for formalin-fixed, paraffin-embedded (FFPE) tissue (i.e., highly degraded tissue). The primers were designed to detect a maximum number of gene transcripts and were designed to be cDNA specific (i.e., not affected by genomic DNA contamination of the total, tissue-derived cDNA). The housekeeping genes, keratin genes, melanocyte-specific genes, and selected high interest genes were detected using four separate and individually designed primer pairs. The primer pairs are set forth in Table 2.

TABLE 2

Primer sets for indicated genes.

| Gene Name | Forward primer | Reverse primer |
|---|---|---|
| ACTB | 5'-GCCAACCGCGAGAAGATG-3'; SEQ ID NO: 1 | 5'-GGCTGGGGTGTTGAAGGT-3'; SEQ ID NO: 2 |
| | 5'-CGCGAGAAGATGACCCAGAT-3'; SEQ ID NO: 3 | 5'-GGGGTGTTGAAGGTCTCAAA-3'; SEQ ID NO: 4 |
| | 5'-TGACCCAGATCATGTTTGAGA-3'; SEQ ID NO: 5 | 5'-GTACATGGCTGGGGTGTTG-3'; SEQ ID NO: 6 |
| | 5'-CTGAACCCCAAGGCCAAC-3'; SEQ ID NO: 7 | 5'-TGATCTGGGTCATCTTCTCG-3'; SEQ ID NO: 8 |
| RPLP0 | 5'-AACTCTGCATTCTCGCTTCC-3'; SEQ ID NO: 9 | 5'-GCAGACAGACACTGGCAACA-3'; SEQ ID NO: 10 |
| | 5'-GCACCATTGAAATCCTGAGTG-3'; SEQ ID NO: 11 | 5'-GCTCCCACTTTGTCTCCAGT-3'; SEQ ID NO: 12 |
| | 5'-TCACAGAGGAAACTCTGCATTC-3'; SEQ ID NO: 13 | 5'-GGACACCCTCCAGGAAGC-3'; SEQ ID NO: 14 |
| | 5'-ATCTCCAGGGGCACCATT-3'; SEQ ID NO: 15 | 5'-AGCTGCACATCACTCAGGATT-3'; SEQ ID NO: 16 |
| RPL8 | 5'-ACTGCTGGCCACGAGTACG-3'; SEQ ID NO: 17 | 5'-ATGCTCCACAGGATTCATGG-3'; SEQ ID NO: 18 |
| | 5'-ACAGAGCTGTGGTTGGTGTG-3'; SEQ ID NO: 19 | 5'-TTGTCAATTCGGCCACCT-3'; SEQ ID NO: 20 |
| | 5'-TATCTCCTCAGCCAACAGAGC-3'; SEQ ID NO: 21 | 5'-AGCCACCACACCAACCAC-3'; SEQ ID NO: 22 |
| | 5'-GTGTGGCCATGAATCCTGT-3'; SEQ ID NO: 23 | 5'-CCACCTCCAAAAGGATGCTC-3'; SEQ ID NO: 24 |
| B2M | 5'-TCTCTCTTTCTGGCCTGGAG-3'; SEQ ID NO: 25 | 5'-GAATCTTTGGAGTACGCTGGA-3'; SEQ ID NO: 26 |
| | 5'-TGGAGGCTATCCAGCGTACT-3'; SEQ ID NO: 27 | 5'-CGTGAGTAAACCTGAATCTTTGG-3'; SEQ ID NO: 28 |
| | 5'-CCAGCGTACTCCAAAGATTCA-3'; SEQ ID NO: 29 | 5'-TCTCTGCTGGATGACGTGAG-3'; SEQ ID NO: 30 |
| | 5'-GGCTATCCAGCGTACTCCAA-3'; SEQ ID NO: 31 | 5'-GCTGGATGACGTGAGTAAACC-3'; SEQ ID NO: 32 |
| KRT14 | 5'-ACCATTGAGGACCTGAGGAA-3'; SEQ ID NO: 33 | 5'-GTCCACTGTGGCTGTGAGAA-3'; SEQ ID NO: 34 |
| | 5'-CATTGAGGACCTGAGGAACA-3'; SEQ ID NO: 35 | 5'-AATCTGCAGAAGGACATTGG-3'; SEQ ID NO: 36 |
| | 5'-GATGACTTCCGCACCAAGTA-3'; SEQ ID NO: 37 | 5'-CGCAGGTTCAACTCTGTCTC-3'; SEQ ID NO: 38 |
| | 5'-TCCGCACCAAGTATGAGACA-3'; SEQ ID NO: 39 | 5'-ACTCATGCGCAGGTTCAACT-3'; SEQ ID NO: 40 |
| KRT10 | 5'-GAGCCTCGTGACTACAGCAA-3'; SEQ ID NO: 41 | 5'-GCAGGATGTTGGCATTATCAGT-3'; SEQ ID NO: 42 |
| | 5'-AAAACCATCGATGACCTTAAAAA-3'; SEQ ID NO: 43 | 5'-GATCTGAAGCAGGATGTTGG-3'; SEQ ID NO: 44 |
| MITF | 5'-TTCCCAAGTCAAATGATCCAG-3'; SEQ ID NO: 45 | 5'-AAGATGGTTCCCTTGTTCCA-3'; SEQ ID NO: 46 |
| | 5'-CGGCATTTGTTGCTCAGAAT-3'; SEQ ID NO: 47 | 5'-GAGCCTGCATTTCAAGTTCC-3'; SEQ ID NO: 48 |
| TYR | 5'-TTCCTTCTTCACCATGCATTT-3'; SEQ ID NO: 49 | 5'-GGAGCCACTGCTCAAAAATA-3'; SEQ ID NO: 50 |
| | 5'-TCCAAAGATCTGGGCTATGA-3'; SEQ ID NO: 51 | 5'-TTGAAAAGAGTCTGGGTCTGAA-3'; SEQ ID NO: 52 |
| MLANA | 5'-GAGAAAAACTGTGAACCTGTGG-3'; SEQ ID NO: 53 | 5'-ATAAGCAGGTGGAGCATTGG-3'; SEQ ID NO: 54 |
| | 5'-GAAGACGAAATGGATACAGAGC-3'; SEQ ID NO: 55 | 5'-GTGCCAACATGAAGACTTTTATC-3'; SEQ ID NO: 56 |

TABLE 2-continued

Primer sets for indicated genes.

| Gene Name | Forward primer | Reverse primer |
|---|---|---|
| PMEL | 5'-GTGGTCAGCACCCAGCTTAT-3';<br>SEQ ID NO: 57<br>5'-GCTGTGGTCCTTGCATCTCT-3';<br>SEQ ID NO: 59 | 5'-CCAAGGCCTGCTTCTTGAC-3';<br>SEQ ID NO: 58<br>5'-GCTTCATAAGTCTGCGCCTA-3';<br>SEQ ID NO: 60 |
| FN1 | 5'-CTCCTGCACATGCTTTGGA-3';<br>SEQ ID NO: 61<br>5'-AGGCTTTGGAAGTGGTCATT-3';<br>SEQ ID NO: 63<br>5'-GAAGTGGTCATTTCAGATGTGATT-3';<br>SEQ ID NO: 65<br>5'-TGGTCATTTCAGATGTGATTCAT-3';<br>SEQ ID NO: 67 | 5'-AGGTCTGCGGCAGTTGTC-3';<br>SEQ ID NO: 62<br>5'-CCATTGTCATGGCACCATCT-3';<br>SEQ ID NO: 64<br>5'-CCATTGTCATGGCACCATCT-3';<br>SEQ ID NO: 66<br>5'-CATTGTCATGGCACCATCTA-3';<br>SEQ ID NO: 68 |
| SPP1 | 5'-GTTTCGCAGACCTGACATCC-3';<br>SEQ ID NO: 69<br>5'-CCTGACATCCAGTACCCTGA-3';<br>SEQ ID NO: 71<br>5'-GAATCTCCTAGCCCCACAGA-3';<br>SEQ ID NO: 73<br>5'-CCCATCTCAGAAGCAGAATCTC-3';<br>SEQ ID NO: 75 | 5'-TCCTCGTCTGTAGCATCAGG-3';<br>SEQ ID NO: 70<br>5'-TGAGGTGATGTCCTCGTCTG-3';<br>SEQ ID NO: 72<br>5'-GGTTTCTTCAGAGGACACAGC-3';<br>SEQ ID NO: 74<br>5'-ACAGCATTCTGTGGGGCTA-3';<br>SEQ ID NO: 76 |
| COL4A1 | 5'-GGAAAACCAGGACCCAGAG-3';<br>SEQ ID NO: 77<br>5'-AGAAAGGTGAACCCGGAAAA-3';<br>SEQ ID NO: 79<br>5'-GAGAAAAGGGCCAAAAAGGT-3';<br>SEQ ID NO: 81<br>5'-AAAGGGCCAAAAAGGTGAAC-3';<br>SEQ ID NO: 83 | 5'-CTTTTTCCCCTTTGTCACCA-3';<br>SEQ ID NO: 78<br>5'-GGTTTGCCTCTGGGTCCT-3';<br>SEQ ID NO: 80<br>5'-CATCCCCTGAAATCCAGGTT-3';<br>SEQ ID NO: 82<br>5'-CCTGGCATCCCCTGAAAT-3';<br>SEQ ID NO: 84 |
| TNC | 5'-GTGTCAACCTGATGGGGAGA-3';<br>SEQ ID NO: 85<br>5'-GGTACAGTGGGACAGCAGGT-3';<br>SEQ ID NO: 87<br>5'-AACCACAGTCAGGGCGTTA-3';<br>SEQ ID NO: 89<br>5'-AAGCTGAAGGTGGAGGGGTA-3';<br>SEQ ID NO: 91 | 5'-GTTAACGCCCTGACTGTGGT-3';<br>SEQ ID NO: 86<br>5'-GATCTGCCATTGTGGTAGGC-3';<br>SEQ ID NO: 88<br>5'-GTTCGTGGCCCTTCCAGT-3';<br>SEQ ID NO: 90<br>5'-GAGTCACCTGCTGTCCCACT-3';<br>SEQ ID NO: 92 |
| ITGA3 | 5'-TATTCCTCCGAACCAGCATC-3';<br>SEQ ID NO: 93<br>5'-CCACCATCAACATGGAGAAC-3';<br>SEQ ID NO: 95 | 5'-CACCAGCTCCGAGTCAATGT-3';<br>SEQ ID NO: 94<br>5'-AGTCAATGTCCACAGAGAACCA-3';<br>SEQ ID NO: 96 |
| LOXL3 | 5'-CAACTGCCACATTGGTGATG-3';<br>SEQ ID NO: 97<br>5'-TGACATCACGGATGTGAAGC-3';<br>SEQ ID NO: 99 | 5'-AAACCTCCTGTTGGCCTCTT-3';<br>SEQ ID NO: 98<br>5'-GGGTTGATGACAACCTGGAG-3';<br>SEQ ID NO: 100 |
| AGRN | 5'-TGTGACCGAGAGCGAGAAG-3';<br>SEQ ID NO: 101<br>5'-CGGACCTTTGTCGAGTACCT-3';<br>SEQ ID NO: 103 | 5'-CAGGCTCAGTTCAAAGTGGTT-3';<br>SEQ ID NO: 102<br>5'-GTTGCTCTGCAGTGCCTTCT-3';<br>SEQ ID NO: 104 |
| VCAN | 5'-GACTTCCGTTGGACTGATGG-3';<br>SEQ ID NO: 105<br>5'-ACGTGCAAGAAAGGAACAGT-3';<br>SEQ ID NO: 107 | 5'-TGGTTGGGTCTCCAATTCTC-3';<br>SEQ ID NO: 106<br>5'-TCCAAAGGTCTTGGCATTTT-3';<br>SEQ ID NO: 108 |
| PLOD3 | 5'-GCAGAGATGGAGCACTACGG-3';<br>SEQ ID NO: 109<br>5'-GGAAGGAATCGTGGAGCAG-3';<br>SEQ ID NO: 111 | 5'-CAGCCTTGAATCCTCATGC-3';<br>SEQ ID NO: 110<br>5'-CAGCAGTGGGAACCAGTACA-3';<br>SEQ ID NO: 112 |
| ITGB1 | 5'-CTGATGAATGAAATGAGGAGGA-3';<br>SEQ ID NO: 113<br>5'-CAGTTTGCTGTGTGTTGCTC-3';<br>SEQ ID NO: 115 | 5'-CACAAATGAGCCAAATCCAA-3';<br>SEQ ID NO: 114<br>5'-CATGATTTGGCATTTGCTTTT-3';<br>SEQ ID NO: 116 |
| PTK2 | 5'-GCCCCACCAGAGGAGTATGT-3';<br>SEQ ID NO: 117<br>5'-GAGACCATTCCCCTCCTACC-3';<br>SEQ ID NO: 119 | 5'-AAGCCGACTTCCTTCACCA-3';<br>SEQ ID NO: 118<br>5'-GCTTCTGTGCCATCTCAATCT-3';<br>SEQ ID NO: 120 |

TABLE 2-continued

Primer sets for indicated genes.

| Gene Name | Forward primer | Reverse primer |
|---|---|---|
| CTGF | 5'-CGAAGCTGACCTGGAAGAGA-3';<br>SEQ ID NO: 121<br>5'-GTGTGCACCGCCAAAGAT-3';<br>SEQ ID NO: 123 | 5'-TGGGAGTACGGATGCACTTT-3';<br>SEQ ID NO: 122<br>5'-CGTACCACCGAAGATGCAG-3';<br>SEQ ID NO: 124 |
| PLOD1 | 5'-CTACCCCGGCTACTACACCA-3';<br>SEQ ID NO: 125<br>5'-AGTCGGGGTGGATTACAGAG-3';<br>SEQ ID NO: 127 | 5'-GACAAAGGCCAGGTCAAACT-3';<br>SEQ ID NO: 126<br>5'-ACAGTTGTAGCGCAGGAACC-3';<br>SEQ ID NO: 128 |
| LAMC1 | 5'-ATGATGATGGCAGGGATGG-3';<br>SEQ ID NO: 129 | 5'-GCATTGATCTCGGCTTCTTG-3';<br>SEQ ID NO: 130 |
| THBS1 | 5'-CTGTGGCACACAGGAAACAC-3';<br>SEQ ID NO: 131<br>5'-GCCAAAGACGGGTTTCATTA-3';<br>SEQ ID NO: 133 | 5'-ACGAGGGTCATGCCACAG-3';<br>SEQ ID NO: 132<br>5'-GCCATGATTTTCTTCCCTTC-3';<br>SEQ ID NO: 134 |
| LOXL2 | 5'-CTCCTCCTACGGCAAGGGA-3';<br>SEQ ID NO: 135<br>5'-CTCCTACGGCAAGGGAGAAG-3';<br>SEQ ID NO: 137 | 5'-TGGAGATTGTCTAACCAGATGGG-3';<br>SEQ ID NO: 136<br>5'-TTGCCAGTACAGTGGAGATTG-3';<br>SEQ ID NO: 138 |
| IL6 | 5'-CCAGAGCTGTCAGATGAGT-3';<br>SEQ ID NO: 139 | 5'-TGCATCTAGATTCTTTGCCTTTT-3';<br>SEQ ID NO: 140 |
| LOXL1 | 5'-AGGGCACAGCAGACTTCCT-3';<br>SEQ ID NO: 141<br>5'-GCATGCACCTCTCATACCC-3';<br>SEQ ID NO: 143 | 5'-TCGTCCATGCTGTGGTAATG-3';<br>SEQ ID NO: 142<br>5'-CGCATTGTAGGTGTCATAGCA-3';<br>SEQ ID NO: 144 |
| IL8 | 5'-CTTGGCAGCCTTCCTGATT-3';<br>SEQ ID NO: 145 | 5'-GCAAAACTGCACCTTCACAC-3';<br>SEQ ID NO: 146 |
| CYR61 | 5'-CGCTCTGAAGGGGATCTG-3';<br>SEQ ID NO: 147<br>5'-GAGCTCAGTCAGAGGGCAGA-3';<br>SEQ ID NO: 149 | 5'-ACAGGGTCTGCCCTCTGACT-3';<br>SEQ ID NO: 148<br>5'-AACTTTCCCCGTTTTGGTAGA-3';<br>SEQ ID NO: 150 |
| ITGAV | 5'-GACCTTGGAAACCCAATGAA-3';<br>SEQ ID NO: 147<br>5'-GGTGGTATGTGACCTTGGAAA-3';<br>SEQ ID NO: 149 | 5'-TCCATCTCTGACTGCTGGTG-3';<br>SEQ ID NO: 148<br>5'-GCACACTGAAACGAAGACCA-3';<br>SEQ ID NO: 150 |
| YAP | 5'-TGAACAGTGTGGATGAGATGG-3';<br>SEQ ID NO: 151 | 5'-GCAGGGTGCTTTGGTTGATA-3';<br>SEQ ID NO: 152 |
| BGN | 5'-AAGGGTCTCCAGCACCTCTAC-3';<br>SEQ ID NO: 153<br>5'-GAGCTCCGCAAGGATGACT-3';<br>SEQ ID NO: 155 | 5'-AAGGCCTTCTCATGGATCTT-3';<br>SEQ ID NO: 154<br>5'-AGGACGAGGGCGTAGAGGT-3';<br>SEQ ID NO: 156 |
| LAMB1 | 5'-CATTCAAGGAACCCAGAACC-3';<br>SEQ ID NO: 157 | 5'-GCGTTGAACAAGGTTTCCTC-3';<br>SEQ ID NO: 158 |
| ITBG3 | 5'-AAGAGCCAGAGTGTCCCAAG-3';<br>SEQ ID NO: 159<br>5'-CTTCTCCTGTGTCCGCTACAA-3';<br>SEQ ID NO: 161<br>5'-TGCCTGCACCTTTAAGAAAGA-3';<br>SEQ ID NO: 163<br>5'-AAGGGGAGATGTGCTCAG-3';<br>SEQ ID NO: 165 | 5'-ACTGAGAGCAGGACCACCA-3';<br>SEQ ID NO: 160<br>5'-CATGGCCTGAGCACATCTC-3';<br>SEQ ID NO: 162<br>5'-CCGGTCAAACTTCTTACACTCC-3';<br>SEQ ID NO: 164<br>5'-CAGTCCCCACAGCTGCAC-3';<br>SEQ ID NO: 166 |
| CXCL1 | 5'-AAACCGAAGTCATAGCCACAC-3';<br>SEQ ID NO: 167 | 5'-AAGCTTTCCGCCCATTCTT-3';<br>SEQ ID NO: 168 |
| THBS2 | 5'-AGGCCCAAGACTGGCTACAT-3';<br>SEQ ID NO: 169<br>5'-GGCAGGTGCGAACCTTATG-3';<br>SEQ ID NO: 171 | 5'-CTGCCATGACCTGTTTTCCT-3';<br>SEQ ID NO: 170<br>5'-CCTTCCAGCCAATGTTCCT-3';<br>SEQ ID NO: 172 |
| COL18A1 | 5'-GATCGCTGAGCTGAAGGTG-3';<br>SEQ ID NO: 173 | 5'-CGGATGCCCCATCTGAGT-3';<br>SEQ ID NO: 174 |

TABLE 2-continued

Primer sets for indicated genes.

| Gene Name | Forward primer | Reverse primer |
|---|---|---|
| SPARC | 5'-CCCATTGGCGAGTTTGAGAAG-3';<br>SEQ ID NO: 175<br>5'-GGAAGAAACTGTGGCAGAGG-3';<br>SEQ ID NO: 177 | 5'-AGGAAGAGTCGAAGGTCTTGTT-3';<br>SEQ ID NO: 176<br>5'-GGACAGGATTAGCTCCCACA-3';<br>SEQ ID NO: 178 |
| TP53 | 5'-ACAACGTTCTGTCCCCCTTG-3';<br>SEQ ID NO: 179 | 5'-GGGGACAGCATCAAATCATC-3';<br>SEQ ID NO: 180 |
| PLOD2 | 5'-TGGATGCAGATGTTGTTTTGA-3';<br>SEQ ID NO: 181<br>5'-TTGATTGAACAAAACAGAAAGATCA-3';<br>SEQ ID NO: 183 | 5'-CACAGCTTTCCATGACGAGTT-3';<br>SEQ ID NO: 182<br>5'-TGACGAGTTACAAGAGGAGCAA-3';<br>SEQ ID NO: 184 |
| CCL2 | 5'-CTGCTCATAGCAGCCACCTT-3';<br>SEQ ID NO: 185 | 5'-AGGTGACTGGGGCATTGATT-3';<br>SEQ ID NO: 186 |
| FBLN2 | 5'-ACGTGGAGGAGGACACAGAC-3';<br>SEQ ID NO: 187 | 5'-GGAGCCTTCAGGGCTACTTC-3';<br>SEQ ID NO: 188 |
| LAMA1 | 5'-AGCACTGCCAAAGTGGATG-3';<br>SEQ ID NO: 189 | 5'-TTGTTGACATGGAACAAGACC-3';<br>SEQ ID NO: 190 |
| THBS4 | 5'-GTGGGCTACATCAGGGTACG-3';<br>SEQ ID NO: 191<br>5'-CATCATCTGGTCCAACCTCA-3';<br>SEQ ID NO: 193 | 5'-CAGAGTCAGCCACCAACTCA-3';<br>SEQ ID NO: 192<br>5'-GTCCTCAGGGATGGTGTCAT-3';<br>SEQ ID NO: 194 |
| COL1A1 | 5'-TGACCTCAAGATGTGCCACT-3';<br>SEQ ID NO: 195<br>5'-GATGGATTCCAGTTCGAGTATG-3';<br>SEQ ID NO: 197 | 5'-TGGTTGGGGTCAATCCAGTA-3';<br>SEQ ID NO: 196<br>5'-ATCAGGCGCAGGAAGGTC-3';<br>SEQ ID NO: 198 |
| ITGA5 | 5'-CCCAAAAAGAGCGTCAGGT-3';<br>SEQ ID NO: 199 | 5'-TTGTTGACATGGAACAAGACC-3';<br>SEQ ID NO: 200 |
| TAZ | 5'-CTTCCTAACAGTCCGCCCTA-3';<br>SEQ ID NO: 201 | 5'-CCCGATCAGCACAGTGATTT-3';<br>SEQ ID NO: 202 |
| POSTN | 5'-CTGCTTCAGGGAGACACACC-3';<br>SEQ ID NO: 203<br>5'-AGGAAGTTGCAAGCCAACAA-3';<br>SEQ ID NO: 205 | 5'-TGGCTTGCAACTTCCTCAC-3';<br>SEQ ID NO: 204<br>5'-CGACCTTCCCTTAATCGTCTT-3';<br>SEQ ID NO: 206 |
| LOX | 5'-GCGGAGGAAAACTGTCTGG-3';<br>SEQ ID NO: 207<br>5'-ATATTCCTGGGAATGGCACA-3';<br>SEQ ID NO: 209 | 5'-AAATCTGAGCAGCACCCTGT-3';<br>SEQ ID NO: 208<br>5'-CCATACTGTGGTAATGTTGATGA-3';<br>SEQ ID NO: 210 |
| CSRC | 5'-TGTCAACAACACAGAGGGAGA-3';<br>SEQ ID NO: 211<br>5'-TGGCAAGATCACCAGACGG-3';<br>SEQ ID NO: 213 | 5'-CACGTAGTTGCTGGGGATGT-3';<br>SEQ ID NO: 212<br>5'-GGCACCTTTCGTGGTCTCAC-3';<br>SEQ ID NO: 214 |
| LAMA3 | 5'-CATGTCGTCTTGGCTCACTC-3';<br>SEQ ID NO: 215 | 5'-AAATTCTGGCCCCAACAATAC-3';<br>SEQ ID NO: 216 |
| CDKN1A | 5'-CATGTCGTCTTGGCTCACTC-3';<br>SEQ ID NO: 217 | 5'-AAATTCTGGCCCCAACAATAC-3';<br>SEQ ID NO: 218 |
| CDKN2A | 5'-AGGAGCCAGCGTCTAGGG-3';<br>SEQ ID NO: 219<br>5'-AACGCACCGAATAGTTACGG-3';<br>SEQ ID NO: 221 | 5'-CTGCCCATCATCATGACCT-3';<br>SEQ ID NO: 220<br>5'-CATCATCATGACCTGGATCG-3';<br>SEQ ID NO: 222 |
| ITGA2 | 5'-CACTGTTACGATTCCCCTGA-3';<br>SEQ ID NO: 223 | 5'-CGGCTTTCTCATCAGGTTTC-3';<br>SEQ ID NO: 224 |
| LAMC2 | 5'-ATTAGACGGCCTCCTGCATC-3';<br>SEQ ID NO: 225 | 5'-AGACCAGCCCCTCTTCATCT-3';<br>SEQ ID NO: 226 |
| PCOLCE2 | 5'-TACTTGGAAAATCACAGTTCCCG-3';<br>SEQ ID NO: 225 | 5'-TGAATCGGAAATTGAGAACGACT-3';<br>SEQ ID NO: 226 |
| LOXL4 | 5'-GGCCCCGGGAATTATATCT-3';<br>SEQ ID NO: 227 | 5'-CCACTTCATAGTGGGGTTC-3';<br>SEQ ID NO: 228 |

TABLE 2-continued

Primer sets for indicated genes.

| Gene Name | Forward primer | Reverse primer |
|---|---|---|
| | 5'-CTGCACAACTGCCACACAG-3';<br>SEQ ID NO: 229 | 5'-GTTCTGCATTGGCTGGGTAT-3';<br>SEQ ID NO: 230 |
| PCOLCE | 5'-CGTGGCAAGTGAGGGGTTC-3';<br>SEQ ID NO: 231<br>5'-GAGGCTTCCTGCTCTGGT-3';<br>SEQ ID NO: 233 | 5'-CGAAGACTCGGAATGAGAGGG-3';<br>SEQ ID NO: 232<br>5'-CGCAAAATTGGTGCTCAGT-3';<br>SEQ ID NO: 234 |
| LAMB3 | 5'-GTCCGGGACTTCCTAACAGA-3';<br>SEQ ID NO: 235 | 5'-GCTGACCTCCTGGATAGTGTG-3';<br>SEQ ID NO: 236 |
| PMEL | 5'-GTGGTCAGCACCCAGCTTAT-3';<br>SEQ ID NO: 237<br>5'-GCTGTGGTCCTTGCATCTCT-3';<br>SEQ ID NO: 239 | 5'-CCAAGGCCTGCTTCTTGAC-3';<br>SEQ ID NO: 238<br>5'-GCTTCATAAGTCTGCGCCTA-3';<br>SEQ ID NO: 240 |
| NES | 5'-CTTCCCTCAGCTTTCAGGAC-3';<br>SEQ ID NO: 241<br>5'-ACCTCAAGATGTCCCTCAGC-3';<br>SEQ ID NO: 243 | 5'-TCTGGGGTCCTAGGGAATTG-3';<br>SEQ ID NO: 242<br>5'-CAGGAGGGTCCTGTACGTG-3';<br>SEQ ID NO: 244 |
| L1CAM | 5'-GAGACCTTCGGCGAGTCACAG-3';<br>SEQ ID NO: 245<br>5'-GGCGGCAAATACTCAGTGAA-3';<br>SEQ ID NO: 247 | 5'-AAAGGCCTTCTCCTCGTTGT-3';<br>SEQ ID NO: 246<br>5'-CCTGGGTGTCCTCCTTATCC-3';<br>SEQ ID NO: 248 |
| GDF15 | 5'-CGGATACTCACGCCAGAAGT-3';<br>SEQ ID NO: 249<br>5'-AAGATTCGAACACCGACCTC-3';<br>SEQ ID NO: 251 | 5'-AGAGATACGCAGGTGCAGGT-3';<br>SEQ ID NO: 250<br>5'-GCACTTCTGGCGTGAGTATC-3';<br>SEQ ID NO: 252 |
| ARPC1B | 5'-CACGCCTGGAACAAGGAC-3';<br>SEQ ID NO: 253<br>5'-CAGGTGACAGGCATCGACT-3';<br>SEQ ID NO: 255 | 5'-ATGCACCTCATGGTTGTTGG-3';<br>SEQ ID NO: 254<br>5'-CGCAGGTCACAATACGGTTA-3';<br>SEQ ID NO: 256 |
| FARP1 | 5'-TGAGGCCCTGAGAGAGAAGA-3';<br>SEQ ID NO: 257<br>5'-TCAAGGAAATTGAGCAACGA-3';<br>SEQ ID NO: 259 | 5'-ATTCCGAAACTCCACACGTC-3';<br>SEQ ID NO: 258<br>5'-TCTGATTTGGGCATTTGAGC-3';<br>SEQ ID NO: 260 |
| NTRK3 | 5'-TATGGTCGACGGTCCAAAT-3';<br>SEQ ID NO: 261<br>5'-CACTGTGACCCACAAACCAG-3';<br>SEQ ID NO: 263 | 5'-TCCTCACCACTGATGACAGC-3';<br>SEQ ID NO: 262<br>5'-GCAAGTCCAACTGCTATGGA-3';<br>SEQ ID NO: 264 |
| CSK | 5'-TGAGGCCCTGAGAGAGAAGA-3';<br>SEQ ID NO: 265<br>5'-TCTACTCCTTTGGGCGAGTG-3';<br>SEQ ID NO: 267 | 5'-ATTCCGAAACTCCACACGTC-3';<br>SEQ ID NO: 266<br>5'-CGTCCTTCAGGGGAATTCTT-3';<br>SEQ ID NO: 268 |
| CD44 | 5'-TAAGGACACCCCAAATTCCA-3';<br>SEQ ID NO: 269<br>5'-GCAGTCAACAGTCGAAGAAGG-3';<br>SEQ ID NO: 271 | 5'-GCCAAGATGATCAGCCATTC-3';<br>SEQ ID NO: 270<br>5'-AGCTTTTTCTTCTGCCCACA-3';<br>SEQ ID NO: 272 |
| SNX17 | 5'-AGCCAGCAAGCAGTGAAGTC-3';<br>SEQ ID NO: 273<br>5'-CCGGGAGTCTATGGTCAAAC-3';<br>SEQ ID NO: 275 | 5'-TCAGGTGACTCAAGCAGTGG-3';<br>SEQ ID NO: 274<br>5'-CACGGCACTCAGCTTACTTG-3';<br>SEQ ID NO: 276 |
| PLAT | 5'-TGGAGCAGTCTTCGTTTCG-3';<br>SEQ ID NO: 277<br>5'-GCCCGATTCAGAAGAGGAG-3';<br>SEQ ID NO: 279 | 5'-CTGGCTCCTCTTCTGAATCG-3';<br>SEQ ID NO: 278<br>5'-TCATCTCTGCAGATCACTTGG-3';<br>SEQ ID NO: 280 |

The following was performed to generate a standard curve for the target of each primer pair. The standard was generated with a defined number of amplicons per volume for each primer pair. In particular, a standard (S7) was designed to contain about 5 million copies of amplicon-containing cDNA in a bacterial expression vector backbone (pJET1.2 obtained from Fermentas) per one microliter volume for each primer pair. From this, six 1:10 dilutions were generated such that seven standards S1 to S7 were obtained ranging from 5 to 5 million copies of amplicon. To obtain fragments of cDNA, total RNA was extracted from the human HaCaT, A431, and A375 cell lines, and the RNA was reverse transcribed into cDNA. Cell line-derived cDNA was used as a template to amplify fragments of cDNA that contained the desired amplicons for the real time-PCR primer pairs. A list of primers used to generate the desired cDNA fragments is listed in Table 3.

TABLE 3

Primer sets for generating cDNA fragments of the indicated genes.

| Gene Name | Forward primer | Reverse primer |
| --- | --- | --- |
| FN1 | 5'-CCAGCAGAGGCATAAGGTTC-3'; SEQ ID NO: 281 | 5'-AGTAGTGCCTTCGGGACTGG-3'; SEQ ID NO: 282 |
| SPP1 | 5'-AGGCTGATTCTGGAAGTTCTGAGG-3'; SEQ ID NO: 283 | 5'-AATCTGGACTGCTTGTGGCTG-3'; SEQ ID NO: 284 |
| COL4A1 | 5'-GTTGGGCCTCCAGGATTTA-3'; SEQ ID NO: 285 | 5'-GCCTGGTAGTCCTGGGAAAC-3'; SEQ ID NO: 286 |
| TNC | 5'-TGGATGGATTGTGTTCCTGA-3'; SEQ ID NO: 287 | 5'-GCCTGCCTTCAAGATTTCTG-3'; SEQ ID NO: 288 |
| ITGA3 | 5'-CTGAGACTGTGCTGACCTGTG-3'; SEQ ID NO: 289 | 5'-CTCTTCATCTCCGCCTTCTG-3'; SEQ ID NO: 290 |
| LOXL3 | 5'-GAGACCGCCTACATCGAAGA-3'; SEQ ID NO: 291 | 5'-GGTAGCGTTCAAACCTCCTG-3'; SEQ ID NO: 292 |
| AGRN | 5'-ACACCGTCCTCAACCTGAAG-3'; SEQ ID NO: 293 | 5'-AATGGCCAGTGCCACATAGT-3'; SEQ ID NO: 294 |
| VCAN | 5'-GGTGCACTTTGTGAGCAAGA-3'; SEQ ID NO: 295 | 5'-TTGGTATGCAGATGGGTTCA-3'; SEQ ID NO: 296 |
| PLOD3 | 5'-AGCTGTGGTCCAACTTCTGG-3'; SEQ ID NO: 297 | 5'-GTGTGGTAACCGGGAAACAG-3'; SEQ ID NO: 298 |
| ITGB1 | 5'-TTCAGTTTGCTGTGTGTTTGC-3'; SEQ ID NO: 299 | 5'-CCACCTTCTGGAGAATCCAA-3'; SEQ ID NO: 300 |
| PTK2 | 5'-GGCAGTATTGACAGGGAGGA-3'; SEQ ID NO: 301 | 5'-TACTCTTGCTGGAGGCTGGT-3'; SEQ ID NO: 302 |
| CTGF | 5'-GCCTATTCTGTCACTTCGGCTC-3'; SEQ ID NO: 303 | 5'-GCAGGCACAGGTCTTGATGAAC-3'; SEQ ID NO: 304 |
| PLOD1 | 5'-GACCTCTGGGAGGTGTTCAG-3'; SEQ ID NO: 305 | 5'-TTAGGGATCGACGAAGGAGA-3'; SEQ ID NO: 306 |
| LAMC1 | 5'-ATTCCTGCCATCAACCAGAC-3'; SEQ ID NO: 307 | 5'-CCTGCTTCTTGGCTTCATTC-3'; SEQ ID NO: 308 |
| THBS1 | 5'-CAAAGGGACATCCCAAAATG-3'; SEQ ID NO: 309 | 5'-GAGTCAGCCATGATTTTCTTCC-3'; SEQ ID NO: 310 |
| LOXL2 | 5'-TACCCCGAGTACTTCCAGCA-3'; SEQ ID NO: 311 | 5'-GATCTGCTTCCAGGTCTTGC-3'; SEQ ID NO: 312 |
| IL6 | 5'-CACACAGACAGCCACTCACC-3'; SEQ ID NO: 313 | 5'-CAGGGGTGGTTATTGCATCT-3'; SEQ ID NO: 314 |
| LOXL1 | 5'-CAGACCCCAACTATGTGCAA-3'; SEQ ID NO: 315 | 5'-CGCATTGTAGGTGTCATAGCA-3'; SEQ ID NO: 316 |
| IL8 | 5'-CTCTCTTGGCAGCCTTCCT-3'; SEQ ID NO: 317 | 5'-TGAATTCTCAGCCCTCTTCAA-3'; SEQ ID NO: 318 |
| CYR61 | 5'-TCGCCTTAGTCGTCACCCTT-3'; SEQ ID NO: 319 | 5'-TGTTTCTCGTCAACTCCACCTCG-3'; SEQ ID NO: 320 |
| ITGAV | 5'-CTGATTTCATCGGGGTTGTC-3'; SEQ ID NO: 321 | 5'-TGCCTTGCTGAATGAACTTG-3'; SEQ ID NO: 322 |

TABLE 3-continued

Primer sets for generating cDNA fragments of the indicated genes.

| Gene Name | Forward primer | Reverse primer |
|---|---|---|
| YAP | 5'-CCAGTGAAACAGCCACCAC-3'; SEQ ID NO: 323 | 5'-CTCCTTCCAGTGTTCCAAGG-3'; SEQ ID NO: 324 |
| BGN | 5'-GGACTCTGTCACACCCACCT-3'; SEQ ID NO: 325 | 5'-CAGGGTCTCAGGGAGGTCTT-3'; SEQ ID NO: 326 |
| LAMB1 | 5'-TGCCAGAGCTGAGATGTTGTT-3'; SEQ ID NO: 327 | 5'-TGTAGCATTTCGGCTTTCCT-3'; SEQ ID NO: 328 |
| ITGB3 | 5'-GGCAAGTACTGCGAGTGTGA-3'; SEQ ID NO: 329 | 5'-ATTCTTTTCGGTCGTGGATG-3'; SEQ ID NO: 330 |
| CXCL1 | 5'-CACTGCTGCTCCTGCTCCT-3'; SEQ ID NO: 331 | 5'-TGTTCAGCATCTTTTCGATGA-3'; SEQ ID NO: 332 |
| THBS2 | 5'-TGACAATGACAACATCCCAGA-3'; SEQ ID NO: 333 | 5'-TGAGTCTGCCATGACCTGTT-3'; SEQ ID NO: 334 |
| COL18A1 | 5'-CCCTGCTCTACACAGAACCAG-3'; SEQ ID NO: 335 | 5'-ACACCTGGCTCCCCTTTCT-3'; SEQ ID NO: 336 |
| SPARC | 5'-GCCTGGATCTTCTTTCTCCTTTGC-3'; SEQ ID NO: 337 | 5'-CATCCAGGGCGATGTACTTGTC-3'; SEQ ID NO: 338 |
| TP53 | 5'-CCCCCTCTGAGTCAGGAAAC-3'; SEQ ID NO: 339 | 5'-TCATGTGCTGTGACTGCTTG-3'; SEQ ID NO: 340 |
| PLOD2 | 5'-TGGACCCACCAAGATTCTCCTG-3'; SEQ ID NO: 341 | 5'-GACCACAGCTTTCCATGACGAG-3'; SEQ ID NO: 342 |
| CCL2 | 5'-TCTGTGCCTGCTGCTCATAG-3'; SEQ ID NO: 343 | 5'-GAGTTTGGGTTTGCTTGTCC-3'; SEQ ID NO: 344 |
| FBLN2 | 5'-CGAGAAGTGCCCAGGAAG-3'; SEQ ID NO: 345 | 5'-AGTGAGAAGCCAGGAAAGCA-3'; SEQ ID NO: 346 |
| LAMA1 | 5'-TGGAAATATCACCCACAGCA-3'; SEQ ID NO: 347 | 5'-AGGCATTTTTGCTTCACACC-3'; SEQ ID NO: 348 |
| THBS4 | 5'-GCTCCAGCTTCTACGTGGTC-3'; SEQ ID NO: 349 | 5'-TTAATTATCGAAGCGGTCGAA-3'; SEQ ID NO: 350 |
| COL1A1 | 5'-AGCCAGCAGATCGAGAACAT-3'; SEQ ID NO: 351 | 5'-CCTTCTTGAGGTTGCCAGTC-3'; SEQ ID NO: 352 |
| ITGA5 | 5'-CACCAATCACCCCATTAACC-3'; SEQ ID NO: 353 | 5'-GCTTGAGCTGAGCTTTTTCC-3'; SEQ ID NO: 354 |
| TAZ | 5'-CCAGGTGCTGGAAAAAGAAG-3'; SEQ ID NO: 355 | 5'-GAGCTGCTCTGCCTGAGTCT-3'; SEQ ID NO: 356 |
| POSTN | 5'-GCAGACACACCTGTTGGAAA-3'; SEQ ID NO: 357 | 5'-GAACGACCTTCCCTTAATCG-3'; SEQ ID NO: 358 |
| LOX | 5'-CCTACTACATCCAGGCGTCCAC-3'; SEQ ID NO: 359 | 5'-ATGCAAATCGCCTGTGGTAGC-3'; SEQ ID NO: 360 |
| CSRC | 5'-CTGTTCGGAGGCTTCAACTC-3'; SEQ ID NO: 361 | 5'-AGGGATCTCCCAGGCATC-3'; SEQ ID NO: 362 |
| LAMA3 | 5'-TACCTGGGATCACCTCCATC-3'; SEQ ID NO: 363 | 5'-ACAGGGATCCTCAGTGTCGT-3'; SEQ ID NO: 364 |
| CDKN1A | 5'-CGGGATGAGTTGGGAGGAG-3'; SEQ ID NO: 365 | 5'-TTAGGGCTTCCTCTTGGAGA-3'; SEQ ID NO: 366 |
| CDKN2A-2A-201 | 5'-0045'-ATGGTGCGCAGGTTCTTG-3'; SEQ ID NO: 367 | 5'-ACCAGCGTGTCCAGGAAG-3'; SEQ ID NO: 368 |
| CDKN2A-2A-202 | 5'-0015'-GAGCAGCATGGAGCCTTC-3'; SEQ ID NO: 369 | 5'-GCATGGTTACTGCCTCTGGT-3'; SEQ ID NO: 370 |
| ITGA2 | 5'-CAAACAGACAAGGCTGGTGA-3'; SEQ ID NO: 371 | 5'-TCAATCTCATCTGGATTTTTGG-3'; SEQ ID NO: 372 |

TABLE 3-continued

Primer sets for generating cDNA fragments of the indicated genes.

| Gene Name | Forward primer | Reverse primer |
| --- | --- | --- |
| LAMC2 | 5'-CTGCAGGTGGACAACAGAAA-3';<br>SEQ ID NO: 373 | 5'-CATCAGCCAGAATCCCATCT-3';<br>SEQ ID NO: 374 |
| PCOLCE2 | 5'-GTCCCCAGAGAGACCTGTTT-3';<br>SEQ ID NO: 375 | 5'-AGACACAATTGGCGCAGGT-3';<br>SEQ ID NO: 376 |
| LOXL4 | 5'-AAGACTGGACGCGATAGCTG-3';<br>SEQ ID NO: 377 | 5'-GGTTGTTCCTGAGACGCTGT-3';<br>SEQ ID NO: 378 |
| PCOLCE | 5'-TACACCAGACCCGTGTTCCT-3';<br>SEQ ID NO: 379 | 5'-TCCAGGTCAAACTTCTCGAAGG-3';<br>SEQ ID NO: 380 |
| LAMB3 | 5'-CTTCAATGCCCAGCTCCA-3';<br>SEQ ID NO: 381 | 5'-TTCCCAACCACATCTTCCAC-3';<br>SEQ ID NO: 382 |
| CSF2 | 5'-CTGCTGCTCTTGGGCACT-3';<br>SEQ ID NO: 383 | 5'-CAGCAGTCAAAGGGGATGAC-3';<br>SEQ ID NO: 384 |
| ACTB | 5'-AGGATTCCTATGTGGGCGACG-3';<br>SEQ ID NO: 385 | 5'-TCAGGCAGCTCGTAGCTCTTC-3';<br>SEQ ID NO: 386 |
| RPLP0 | 5'-GGAATGTGGGCTTTGTGTTCACC-3';<br>SEQ ID NO: 387 | 5'-AGGCCAGGACTCGTTTGTACC-3';<br>SEQ ID NO: 388 |
| RLP8 | 5'-ACATCAAGGGCATCGTCAAGG-3';<br>SEQ ID NO: 389 | 5'-TCTCTTTCTCCTGCACAGTCTTGG-3';<br>SEQ ID NO: 390 |
| B2M | 5'-TGCTCGCGCTACTCTCTCTTTC-3';<br>SEQ ID NO: 391 | 5'-TCACATGGTTCACACGGCAG-3';<br>SEQ ID NO: 392 |
| K10 | 5'-TGGCCTTCTCTCTGGAAATG-3';<br>SEQ ID NO: 393 | 5'-TCATTTCCTCCTCGTGGTTC-3';<br>SEQ ID NO: 394 |
| K14 | 5'-AGGTGACCATGCAGAACCTC-3';<br>SEQ ID NO: 395 | 5'-CCTCGTGGTTCTTCTTCAGG-3';<br>SEQ ID NO: 396 |
| MITF | 5'-GAAATCTTGGGCTTGATGGA-3';<br>SEQ ID NO: 397 | 5'-CCGAGGTTGTTGTTGAAGGT-3';<br>SEQ ID NO: 398 |
| TYR | 5'-CCATGGATAAAGCTGCCAAT-3';<br>SEQ ID NO: 399 | 5'-GACACAGCAAGCTCACAAGC-3';<br>SEQ ID NO: 400 |
| MLANA | 5'-CACTCTTACACCACGGCTGA-3';<br>SEQ ID NO: 401 | 5'-CATAAGCAGGTGGAGCATTG-3';<br>SEQ ID NO: 402 |
| PMEL | 5'-TTGTCCAGGGTATTGAAAGTGC-3';<br>SEQ ID NO: 403 | 5'-GACAAGAGCAGAAGATGCGGG-3';<br>SEQ ID NO: 404 |
| NES | 5'-GCGTTGGAACAGAGGTTGGAG-3';<br>SEQ ID NO: 405 | 5'-CAGGTGTCTCAAGGGTAGCAGG-3';<br>SEQ ID NO: 406 |
| L1CAM | 5'-CTTCCCTTTCGCCACAGTATG-3';<br>SEQ ID NO: 407 | 5'-CCTCCTTCTCCTTCTTGCCACT-3';<br>SEQ ID NO: 408 |
| GDF15 | 5'-AATGGCTCTCAGATGCTCCTGG-3';<br>SEQ ID NO: 409 | 5'-GATTCTGCCAGCAGTTGGTCC-3';<br>SEQ ID NO: 410 |
| ARPC1B | 5'-ACCACAGCTTCCTGGTGGAG-3';<br>SEQ ID NO: 411 | 5'-GAGCGGATGGGCTTCTTGATG-3';<br>SEQ ID NO: 412 |
| FARP1 | 5'-AACGTGACCTTGTCTCCCAAC-3';<br>SEQ ID NO: 413 | 5'-GCATGACATCGCCGATTCTT-3';<br>SEQ ID NO: 414 |
| NTRK3 | 5'-TTCAACAAGCCCACCCACTAC-3';<br>SEQ ID NO: 415 | 5'-GTTCTCAATGACAGGGATGCG-3';<br>SEQ ID NO: 416 |
| CSK | 5'-CATGGAATACCTGGAGGGCAAC-3';<br>SEQ ID NO: 417 | 5'-CAGGTGCCAGCAGTTCTTCAT-3';<br>SEQ ID NO: 418 |
| CD44 | 5'-TCTCAGAGCTTCTCTACATCAC-3';<br>SEQ ID NO: 419 | 5'-CTGACGACTCCTTGTTCACCA-3';<br>SEQ ID NO: 420 |

TABLE 3-continued

Primer sets for generating cDNA fragments of the indicated genes.

| Gene Name | Forward primer | Reverse primer |
|---|---|---|
| SNX17 | 5'-TCACCTCCTCTGTACCATTGC-3'; SEQ ID NO: 421 | 5'-CTCATCTCCAATGCCCTCGA-3'; SEQ ID NO: 422 |
| PLAT | 5'-TGCAATGAAGAGAGGGCTCTG-3'; SEQ ID NO: 432 | 5'-CGTGGCCCTGGTATCTATTTCA-3'; SEQ ID NO: 424 |

The PCR reactions were performed using a high-fidelity polymerase (product name: "Phusion," obtained from New England Biolabs). PCR amplification products were checked for correct size and subsequently gel purified using the Qiagen Gel Extraction kit. Purified PCR fragments were subcloned into the bacterial expression vector pJET1.2 using a commercially available kit (Fermentas). The subcloned fragments were subsequently checked by restriction digest and DNA sequencing. Bacterial clones harboring the pJET1.2 expression vector with the correct PCR insert (containing the desired amplicon for real time PCR primer pairs) were frozen and stored at −80° C. This was done to regenerate the same real time PCR standards over time.

Bacteria harboring the pJET1.2 expression vector with PCR inserts were cultured to generate sufficient amounts of vector. A small aliquot of the total retrieved expression vector with insert was linearized using the PvuI-HF restriction enzyme (from New England Biolabs). The digest was then purified using the Qiagen PCR purification kit. Linearized cDNA was diluted to a concentration of 20 ng/μL. One μL of each of a total of 71 linearized cDNA fragments (each at a 20 ng/μL concentration) were mixed and brought to a final volume of 1 mL to obtain standard S7.

Standard S7 was then diluted six times at a 1:10 ratio to obtained standards S1 to S6. Dilution was performed using ultrapure water obtained from Promega (Cat. No. P1193).

The following was performed to generate cDNA from FFPE samples. FFPE blocks were cut at 20 μm sections using a standard Leica microtome. For large pieces of tissue, 2×20 μm full sections were used for RNA retrieval. For smaller tissues, up to 5×20 μm sections were combined for RNA retrieval. RNA extraction was performed using the Qiagen RNA FFPE retrieval kit and a Qiagen QiaCube extraction robot. 0.5 to 1 μg of RNA with a 260/280 ratio of greater than 1.8 were transcribed into cDNA using the BioRad iScript cDNA Synthesis kit. All biospecimens were annotated with clinical data from Mayo Clinic databases. H&E stained sections were obtained for each block analyzed and digitalized using a high-resolution slide scanner.

Fluidigm RT-PCR was performed using a 96×96 format for high throughput analysis (i.e., 96 cDNAs were analyzed for 96 markers; 9216 data points). The primer pairs and cDNAs were prepared in a 96 well format. Standard curves were calculated for each primer pair. Copy numbers per 100,000 housekeeping genes were calculated for each primer pair and averaged per gene. This was initially done for cDNAs derived from FFPE-embedded skin. To correct for epidermal cell-derived cross-contamination, background signal per one copy of K14 (a basal keratinocyte marker) was calculated from FFPE-embedded normal skin samples for each primer pair and averaged. Experimental samples were then normalized first to 100,000 housekeeping genes and then background-corrected for epidermal cross-contamination based on K14 copy number. In particular, the keratinocyte correction factor used for each gene is set forth in Table E under the column titled "AVG per copy K14."

The study design (Example 1) involved a comparison of the expression profile of "true" benign pigmented skin lesions (nevi, n=73) with "true" malignant melanomas of the skin. The latter comprised i) primary skin melanomas that were documented to metastasize, either to regional lymph nodes, to other areas of skin (in-transit), or to other organs; and ii) in-transit or comparison of nevi to in-transit melanoma metastases (n=54).

Tables C and D summarize the comparisons of the gene expressions between the 73 benign and 54 metastatic. Table A compares the ranked values using the Wilcoxon rank sum test, and Table E compares the dichotomized values (zero vs. >0) using the chi-square test.

A recursive partitioning approach was used to identify cut-points for the genes that would discriminate between these two groups. After partitioning the data at a cut-point of 45 for FN1, no further additional splits in the data based on the other genes were identified by this method.

Using a cutoff of 45 for FN1, the sensitivity was 92.6%, and the specificity was 98.6%. These results are provided in Tables 4 and 5 along with the next possible cutoff for FN1 at 124.

TABLE 4

| Frequency Percent Row Pct Col Pct | Malignant | Benign | Total |
|---|---|---|---|
| FN1 < 45 | 4 | 72 | 76 |
| | 3.15 | 56.69 | 59.84 |
| | 5.26 | 94.74 | |
| | 7.41 | 98.63 | |
| FN1 ≥ 45 | 50 | 1 | 51 |
| | 39.37 | 0.79 | 40.16 |
| | 98.04 | 1.96 | |
| | 92.59 | 1.37 | |
| Total | 54 | 73 | 127 |
| | 42.52 | 57.48 | 100.00 |

TABLE 5

| Frequency Percent Row Pct Col Pct | Malignant | Benign | Total |
|---|---|---|---|
| FN1 < 124 | 8 | 73 | 81 |
| | 6.30 | 57.48 | 63.78 |
| | 9.88 | 90.12 | |
| | 14.81 | 100.00 | |

TABLE 5-continued

| Frequency Percent Row Pct Col Pct | Malignant | Benign | Total |
|---|---|---|---|
| FN1 ≥ 124 | 46<br>36.22<br>100.00<br>85.19 | 0<br>0.00<br>0.00<br>0.00 | 46<br>36.22 |
| Total | 54<br>42.52 | 73<br>57.48 | 127<br>100.00 |

The ability to further discriminate between the groups was assessed by considering SPP1 or ITGB3 in addition to FN1.

Benign Vs. Malignant—Option 1 Using FN1 and SPP1 (FIG. 5)

The results are set forth in Table 6.

TABLE 6

Figure 5:
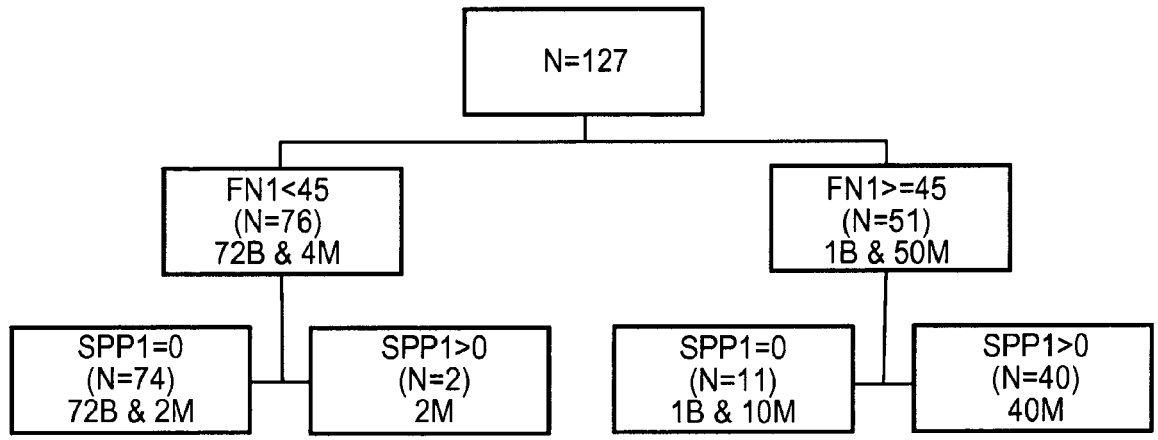
FIG. 5 is a flow chart of an exemplary process for using FN1 and SPP1 expression levels to determine the benign or malignant nature of a skin lesion.

| RULE for FIG. 5 | Malignant | Benign |
|---|---|---|
| FN1 < 45 and SPP1 = 0 | 2 | 72 |
| FN1 ≥ 45<br>or<br>(FN1 < 45 and SPP1 > 0) | 52 | 1 |
| Total | 54 | 73 |

Benign Vs. Malignant—Option 2 Using FN1 and ITGB3 (FIG. 6)

The results are set forth in Table 7.

TABLE 7

Figure 6:
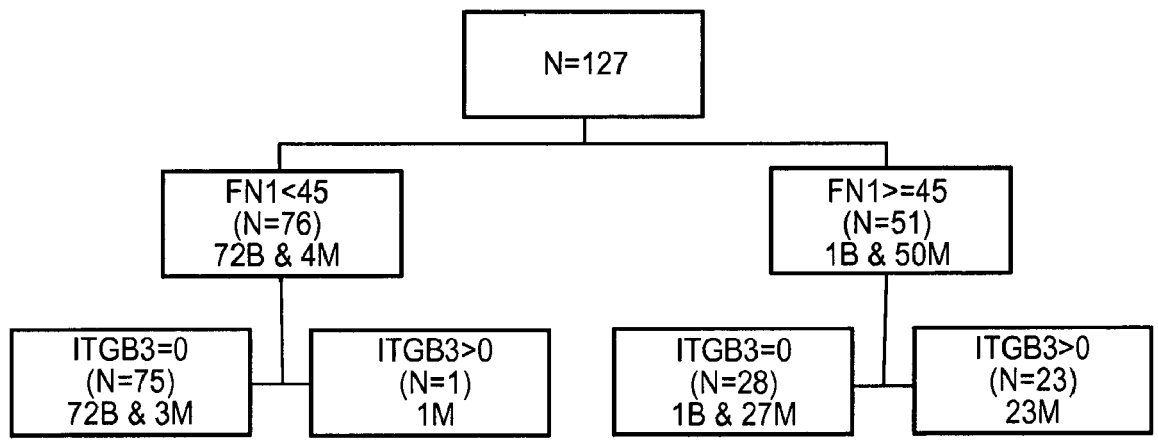
FIG. 6 is a flow chart of an exemplary process for using FN1 and ITGB3 expression levels to determine the benign or malignant nature of a skin lesion.

| RULE for FIG. 6 | Malignant | Benign |
|---|---|---|
| FN1 < 45 and ITGB3 = 0 | 3 | 72 |
| FN1 ≥ 45<br>or<br>(FN1 < 45 and ITGB3 > 0) | 51 | 1 |
| Total | 54 | 73 |

If all three genes are included, the rule was as follows:
FN1<45 and SPP1=0 and ITGB3=0 denotes a negative test
vs.
all other combinations denotes a positive test.

This rule resulted in a specificity of 72/73 (98.6%), and a sensitivity of 53/54 (98.2%) (Table 8). Compared to a rule using FN1 alone, the specificity stayed the same but the sensitivity increased from 92.6% to 98.2% using this new rule.

TABLE 8

| FN1 | SPP1 | ITGB3 | malignant | Frequency | |
|---|---|---|---|---|---|
| <45 | Zero | Zero | No | 72 | |
| <45 | Zero | Zero | Yes | 1 | False Neg ID MM150 (case added from the Breslow file) |
| ≥45 | Zero | Zero | No | 1 | False Pos ID N29 |
| ≥45 | Zero | Zero | Yes | 9 | |
| ≥45 | Zero | >0 | Yes | 1 | |
| ≥45 | >0 | Zero | Yes | 18 | |
| ≥45 | >0 | >0 | Yes | 22 | |
| <45 | Zero | >0 | Yes | 1 | |
| <45 | >0 | Zero | Yes | 2 | |

The rule was evaluated using 25 additional malignant patients who did not have mets (from the "Breslow" file). For 19 of these 25 patients, the rule was "negative" (Table 9).

TABLE 9

| FN1 | SPP1 | ITGB3 | Frequency |
|---|---|---|---|
| <45 | Zero | Zero | 19 |
| <45 | >0 | Zero | 1 |
| ≥45 | Zero | Zero | 2 |
| ≥45 | >0 | Zero | 3 |
| <45 | | | 1 |

The rule also was evaluated using 33 thin melanomas (Table 10). For 25 of these 33 patients, the rule was "negative."

TABLE 10

| FN1 | SPP1 | ITGB3 | Frequency |
|---|---|---|---|
| <45 | Zero | Zero | 25 |
| <45 | Zero | >0 | 1 |
| ≥45 | Zero | Zero | 5 |
| ≥45 | >0 | Zero | 2 |

TABLE C

Comparison of gene expression between benign and malignant

| | Benign (N = 73) | Malignant (N = 54) | p value |
|---|---|---|---|
| CXCL1_AVG_NORM | | | <0.0001 |
| N | 73 | 54 | |
| Mean (SD) | 4.8 (18.4) | 20.0 (26.1) | |
| Median | 0.0 | 10.3 | |
| Q1, Q3 | 0.0, 0.0 | 0.3, 31.1 | |
| Range | (0.0-141.7) | (0.0-120.4) | |
| CSF2_AVG_NORM | | | 0.0482 |
| N | 73 | 54 | |
| Mean (SD) | 10.5 (44.1) | 4.3 (8.4) | |
| Median | 2.5 | 1.0 | |
| Q1, Q3 | 0.6, 7.0 | 0.0, 4.0 | |
| Range | (0.0-375.0) | (0.0-41.0) | |

TABLE C-continued

Comparison of gene expression between benign and malignant

|  | Benign (N = 73) | Malignant (N = 54) | p value |
|---|---|---|---|
| CCL2_AVG_NORM |  |  | <0.0001 |
| N | 73 | 54 |  |
| Mean (SD) | 37.0 (99.4) | 244.2 (360.9) |  |
| Median | 0.0 | 112.8 |  |
| Q1, Q3 | 0.0, 9.1 | 7.2, 342.2 |  |
| Range | (0.0-572.0) | (0.0-1777.1) |  |
| IL8_AVG_NORM |  |  | <0.0001 |
| N | 73 | 54 |  |
| Mean (SD) | 125.5 (671.3) | 53.2 (160.8) |  |
| Median | 0.0 | 13.0 |  |
| Q1, Q3 | 0.0, 0.0 | 2.1, 52.5 |  |
| Range | (0.0-5058.7) | (0.0-1171.7) |  |
| IL6_AVG_NORM |  |  | <0.0001 |
| N | 73 | 54 |  |
| Mean (SD) | 9.9 (69.1) | 21.6 (35.0) |  |
| Median | 0.0 | 8.8 |  |
| Q1, Q3 | 0.0, 0.0 | 0.3, 25.2 |  |
| Range | (0.0-589.1) | (0.0-152.3) |  |
| ITGA5_AVG_NORM |  |  | <0.0001 |
| N | 73 | 54 |  |
| Mean (SD) | 0.0 (0.0) | 9.8 (26.8) |  |
| Median | 0.0 | 0.0 |  |
| Q1, Q3 | 0.0, 0.0 | 0.0, 7.0 |  |
| Range | (0.0-0.0) | (0.0-168.0) |  |
| ITGA3_AVG_NORM |  |  | <0.0001 |
| N | 73 | 54 |  |
| Mean (SD) | 3.2 (27.5) | 168.2 (313.4) |  |
| Median | 0.0 | 50.2 |  |
| Q1, Q3 | 0.0, 0.0 | 2.0, 160.5 |  |
| Range | (0.0-235.4) | (0.0-1506.0) |  |
| ITGA2_AVG_NORM |  |  | 0.0007 |
| N | 73 | 54 |  |
| Mean (SD) | 0.0 (0.0) | 2.6 (10.0) |  |
| Median | 0.0 | 0.0 |  |
| Q1, Q3 | 0.0, 0.0 | 0.0, 0.0 |  |
| Range | (0.0-0.0) | (0.0-69.7) |  |
| ITGAV_AVG_NORM |  |  | <0.0001 |
| N | 73 | 54 |  |
| Mean (SD) | 3.3 (23.9) | 22.0 (32.9) |  |
| Median | 0.0 | 8.0 |  |
| Q1, Q3 | 0.0, 0.0 | 0.0, 31.0 |  |
| Range | (0.0-199.9) | (0.0-176.8) |  |
| ITGB3_AVG_NORM |  |  | <0.0001 |
| N | 73 | 54 |  |
| Mean (SD) | 0.0 (0.0) | 43.6 (90.3) |  |
| Median | 0.0 | 0.0 |  |
| Q1, Q3 | 0.0, 0.0 | 0.0, 52.5 |  |
| Range | (0.0-0.0) | (0.0-495.3) |  |
| ITGB1_AVG_NORM |  |  | <0.0001 |
| N | 73 | 54 |  |
| Mean (SD) | 29.9 (95.1) | 616.2 (742.2) |  |
| Median | 0.0 | 400.2 |  |
| Q1, Q3 | 0.0, 0.0 | 84.7, 869.0 |  |
| Range | (0.0-487.9) | (0.0-3877.9) |  |
| FN1_AVG_NORM |  |  | <0.0001 |
| N | 73 | 54 |  |
| Mean (SD) | 2.9 (15.6) | 1570.9 (1949.8) |  |
| Median | 0.0 | 898.4 |  |
| Q1, Q3 | 0.0, 0.0 | 299.5, 2186.1 |  |
| Range | (0.0-123.2) | (0.0-11073.5) |  |
| THBS1_AVG_NORM |  |  | <0.0001 |
| N | 73 | 54 |  |
| Mean (SD) | 0.0 (0.0) | 85.1 (136.1) |  |
| Median | 0.0 | 16.8 |  |
| Q1, Q3 | 0.0, 0.0 | 0.0, 153.8 |  |
| Range | (0.0-0.0) | (0.0-786.2) |  |
| THBS2_AVG_NORM |  |  | <0.0001 |
| N | 73 | 54 |  |
| Mean (SD) | 25.9 (113.4) | 280.0 (513.5) |  |
| Median | 0.0 | 44.1 |  |
| Q1, Q3 | 0.0, 0.0 | 0.0, 340.1 |  |
| Range | (0.0-729.2) | (0.0-3030.5) |  |
| THBS4_AVG_NORM |  |  | <0.0001 |
| N | 73 | 54 |  |
| Mean (SD) | 38.5 (151.2) | 228.2 (663.7) |  |
| Median | 0.0 | 22.5 |  |

TABLE C-continued

Comparison of gene expression between benign and malignant

| | Benign (N = 73) | Malignant (N = 54) | p value |
|---|---|---|---|
| Q1, Q3 | 0.0, 0.0 | 0.0, 97.9 | |
| Range | (0.0-1130.3) | (0.0-3977.7) | |
| VCAN_AVG_NORM | | | <0.0001 |
| N | 73 | 54 | |
| Mean (SD) | 3.0 (21.7) | 202.4 (262.8) | |
| Median | 0.0 | 103.4 | |
| Q1, Q3 | 0.0, 0.0 | 0.0, 283.5 | |
| Range | (0.0-181.3) | (0.0-1113.2) | |
| BGAN_AVG_NORM | | | <0.0001 |
| N | 73 | 54 | |
| Mean (SD) | 69.3 (121.0) | 422.4 (573.1) | |
| Median | 0.0 | 248.5 | |
| Q1, Q3 | 0.0, 97.9 | 113.5, 462.9 | |
| Range | (0.0-496.3) | (0.0-3348.1) | |
| SPP1_AVG_NORM | | | <0.0001 |
| N | 73 | 54 | |
| Mean (SD) | 0.0 (0.0) | 1490.2 (3397.4) | |
| Median | 0.0 | 338.1 | |
| Q1, Q3 | 0.0, 0.0 | 4.9, 1577.7 | |
| Range | (0.0-0.0) | (0.0-22427.0) | |
| TNC_AVG_NORM | | | <0.0001 |
| N | 73 | 54 | |
| Mean (SD) | 66.4 (240.1) | 800.1 (808.7) | |
| Median | 0.0 | 495.8 | |
| Q1, Q3 | 0.0, 0.0 | 174.5, 1322.9 | |
| Range | (0.0-1393.3) | (0.0-3162.2) | |
| SPARC_AVG_NORM | | | <0.0001 |
| N | 73 | 54 | |
| Mean (SD) | 843.7 (2222.8) | 3208.4 (3182.6) | |
| Median | 0.0 | 2895.8 | |
| Q1, Q3 | 0.0, 0.0 | 407.2, 5216.3 | |
| Range | (0.0-11175.6) | (0.0-13631.9) | |
| AGRN_AVG_NORM | | | <0.0001 |
| N | 73 | 54 | |
| Mean (SD) | 4.7 (18.1) | 51.2 (53.8) | |
| Median | 0.0 | 42.1 | |
| Q1, Q3 | 0.0, 0.0 | 10.7, 69.7 | |
| Range | (0.0-121.7) | (0.0-242.0) | |
| CTGF_AVG_NORM | | | <0.0001 |
| N | 73 | 54 | |
| Mean (SD) | 0.4 (3.6) | 90.9 (231.6) | |
| Median | 0.0 | 22.1 | |
| Q1, Q3 | 0.0, 0.0 | 0.0, 125.9 | |
| Range | (0.0-30.6) | (0.0-1631.4) | |
| CYR61_AVG_NORM | | | <0.0001 |
| N | 73 | 54 | |
| Mean (SD) | 4.8 (13.0) | 27.2 (39.2) | |
| Median | 0.0 | 18.7 | |
| Q1, Q3 | 0.0, 0.0 | 4.9, 32.2 | |
| Range | (0.0-70.4) | (0.0-267.2) | |
| LAMA3_AVG_NORM | | | 0.0004 |
| N | 73 | 54 | |
| Mean (SD) | 1.1 (9.0) | 1.2 (2.9) | |
| Median | 0.0 | 0.0 | |
| Q1, Q3 | 0.0, 0.0 | 0.0, 0.0 | |
| Range | (0.0-76.8) | (0.0-11.3) | |
| LAMC1_AVG_NORM | | | <0.0001 |
| N | 73 | 54 | |
| Mean (SD) | 0.0 (0.0) | 70.6 (159.4) | |
| Median | 0.0 | 28.4 | |
| Q1, Q3 | 0.0, 0.0 | 0.0, 99.3 | |
| Range | (0.0-0.0) | (0.0-1136.2) | |
| LAMB1_AVG_NORM | | | <0.0001 |
| N | 73 | 54 | |
| Mean (SD) | 9.2 (38.4) | 221.1 (354.3) | |
| Median | 0.0 | 73.1 | |
| Q1, Q3 | 0.0, 0.0 | 0.0, 339.8 | |
| Range | (0.0-248.8) | (0.0-1877.6) | |
| LAMA1_AVG_NORM | | | <0.0001 |
| N | 73 | 54 | |
| Mean (SD) | 5.7 (14.5) | 65.4 (149.0) | |
| Median | <0.0 | 10.6 | |
| Q1, Q3 | 0.0, 0.0 | 0.0, 49.0 | |
| Range | (0.0-76.5) | (0.0-754.3) | |

TABLE C-continued

Comparison of gene expression between benign and malignant

| | Benign (N = 73) | Malignant (N = 54) | p value |
|---|---|---|---|
| LAMC2_AVG_NORM | | | 0.0003 |
| N | 73 | 54 | |
| Mean (SD) | 0.0 (0.0) | 4.0 (15.3) | |
| Median | 0.0 | 0.0 | |
| Q1, Q3 | 0.0, 0.0 | 0.0, 0.0 | |
| Range | (0.0-0.0) | (0.0-91.1) | |
| LAMB3_AVG_NORM | | | 0.1473 |
| N | 73 | 54 | |
| Mean (SD) | 33.5 (60.3) | 32.2 (54.5) | |
| Median | 0.0 | 12.1 | |
| Q1, Q3 | 0.0, 44.6 | 0.0, 37.0 | |
| Range | (0.0-323.9) | (0.0-246.0) | |
| COL1A1_AVG_NORM | | | <0.0001 |
| N | 73 | 54 | |
| Mean (SD) | 1534.4 (4365.3) | 4191.6 (5865.9) | |
| Median | 0.0 | 1704.4 | |
| Q1, Q3 | 0.0, 0.0 | 0.0, 6850.9 | |
| Range | (0.0-22510.2) | (0.0-31867.0) | |
| COL4A1_AVG_NORM | | | <0.0001 |
| N | 73 | 54 | |
| Mean (SD) | 0.0 (0.0) | 211.8 (344.1) | |
| Median | 0.0 | 118.4 | |
| Q1, Q3 | 0.0, 0.0 | 2.3, 261.2 | |
| Range | (0.0-0.0) | (0.0-1774.4) | |
| COL18A1_AVG_NORM | | | <0.0001 |
| N | 73 | 54 | |
| Mean (SD) | 94.2 (783.4) | 22.8 (38.8) | |
| Median | 0.0 | 4.1 | |
| Q1, Q3 | 0.0, 0.0 | 0.0, 34.4 | |
| Range | (0.0-6695.7) | (0.0-208.8) | |
| LOX_AVG_NORM | | | 0.0003 |
| N | 73 | 54 | |
| Mean (SD) | 37.7 (132.8) | 65.0 (113.9) | |
| Median | 0.0 | 3.5 | |
| Q1, Q3 | 0.0, 0.0 | 0.0, 58.0 | |
| Range | (0.0-991.2) | (0.0-443.3) | |
| LOXL1_AVG_NORM | | | <0.0001 |
| N | 73 | 54 | |
| Mean (SD) | 0.8 (7.1) | 39.6 (60.3) | |
| Median | 0.0 | 18.5 | |
| Q1, Q3 | 0.0, 0.0 | 0.0, 65.0 | |
| Range | (0.0-60.4) | (0.0-349.0) | |
| LOXL2_AVG_NORM | | | <0.0001 |
| N | 73 | 54 | |
| Mean (SD) | 43.3 (356.8) | 68.5 (129.9) | |
| Median | 0.0 | 22.1 | |
| Q1, Q3 | 0.0, 0.0 | 0.0, 89.1 | |
| Range | (0.0-3048.4) | (0.0-821.4) | |
| LOXL3_AVG_NORM | | | <0.0001 |
| N | 73 | 54 | |
| Mean (SD) | 2.2 (12.3) | 28.4 (71.1) | |
| Median | 0.0 | 9.2 | |
| Q1, Q3 | 0.0, 0.0 | 2.5, 29.4 | |
| Range | (0.0-89.7) | (0.0-507.5) | |
| LOXL4_AVG_NORM | | | 0.0010 |
| N | 73 | 54 | |
| Mean (SD) | 33.8 (91.0) | 129.1 (300.4) | |
| Median | 0.0 | 9.1 | |
| Q1, Q3 | 0.0, 10.2 | 0.0, 67.0 | |
| Range | (0.0-529.2) | (0.0-1230.0) | |
| PLOD1_AVG_NORM | | | <0.0001 |
| N | 73 | 54 | |
| Mean (SD) | 33.7 (116.5) | 420.3 (532.2) | |
| Median | 0.0 | 242.3 | |
| Q1, Q3 | 0.0, 0.0 | 90.2, 659.3 | |
| Range | (0.0-878.2) | (0.0-3336.8) | |
| PLOD2_AVG_NORM | | | <0.0001 |
| N | 73 | 54 | |
| Mean (SD) | 44.5 (151.7) | 314.8 (1284.4) | |
| Median | 0.0 | 53.7 | |
| Q1, Q3 | 0.0, 0.0 | 2.3, 103.3 | |
| Range | (0.0-1124.0) | (0.0-9110.5) | |
| PLOD3_AVG_NORM | | | <0.0001 |
| N | 73 | 54 | |
| Mean (SD) | 2.7 (11.9) | 68.0 (81.2) | |
| Median | 0.0 | 38.3 | |

TABLE C-continued

Comparison of gene expression between benign and malignant

| | Benign (N = 73) | Malignant (N = 54) | p value |
|---|---|---|---|
| Q1, Q3 | 0.0, 0.0 | 4.2, 101.9 | |
| Range | (0.0-87.4) | (0.0-330.2) | |
| PCOLCE2_AVG_NORM | | | 0.0010 |
| N | 73 | 54 | |
| Mean (SD) | 7.7 (25.8) | 6.4 (14.9) | |
| Median | 0.0 | 0.0 | |
| Q1, Q3 | 0.0, 0.0 | 0.0, 3.1 | |
| Range | (0.0-104.8) | (0.0-68.4) | |
| PCOLCE_AVG_NORM | | | 0.0232 |
| N | 73 | 54 | |
| Mean (SD) | 92.1 (159.7) | 170.4 (339.4) | |
| Median | 0.0 | 40.9 | |
| Q1, Q3 | 0.0, 122.2 | 0.0, 175.1 | |
| Range | (0.0-699.2) | (0.0-1945.2) | |
| PTK2_AVG_NORM | | | <0.0001 |
| N | 73 | 54 | |
| Mean (SD) | 2.8 (14.4) | 76.6 (81.8) | |
| Median | 0.0 | 70.0 | |
| Q1, Q3 | 0.0, 0.0 | 0.0, 127.7 | |
| Range | (0.0-116.5) | (0.0-323.3) | |
| CSRC_AVG_NORM | | | 0.0001 |
| N | 73 | 54 | |
| Mean (SD) | 19.0 (40.9) | 45.1 (65.9) | |
| Median | 0.3 | 19.6 | |
| Q1, Q3 | 0.0, 24.8 | 4.2, 46.6 | |
| Range | (0.0-266.6) | (0.0-290.2) | |
| CDKN1A_AVG_NORM | | | 0.0005 |
| N | 73 | 54 | |
| Mean (SD) | 78.5 (150.9) | 181.0 (271.7) | |
| Median | 0.0 | 84.2 | |
| Q1, Q3 | 0.0, 118.9 | 0.0, 253.3 | |
| Range | (0.0-788.2) | (0.0-1083.2) | |
| CDKN2A_AVG_NORM | | | 0.0002 |
| N | 73 | 54 | |
| Mean (SD) | 6.1 (19.6) | 9.7 (25.8) | |
| Median | 0.0 | 1.0 | |
| Q1, Q3 | 0.0, 0.0 | 0.0, 6.9 | |
| Range | (0.0-113.2) | (0.0-175.1) | |
| TP53_AVG_NORM | | | <0.0001 |
| N | 73 | 54 | |
| Mean (SD) | 40.6 (98.6) | 231.2 (289.8) | |
| Median | 0.0 | 166.9 | |
| Q1, Q3 | 0.0, 0.0 | 0.0, 359.9 | |
| Range | (0.0-410.8) | (0.0-1722.4) | |
| YAP_AVG_NORM | | | <0.0001 |
| N | 73 | 54 | |
| Mean (SD) | 7.8 (36.6) | 112.4 (161.4) | |
| Median | 0.0 | 63.1 | |
| Q1, Q3 | 0.0, 0.0 | 0.0, 173.5 | |
| Range | (0.0-246.3) | (0.0-769.0) | |
| TAZ_AVG_NORM | | | <0.0001 |
| N | 73 | 54 | |
| Mean (SD) | 12.2 (27.9) | 32.8 (44.3) | |
| Median | 0.0 | 15.0 | |
| Q1, Q3 | 0.0, 0.7 | 0.0, 49.0 | |
| Range | (0.0-122.7) | (0.0-186.4) | |
| MITF_AVG_NORM | | | <0.0001 |
| N | 73 | 54 | |
| Mean (SD) | 251.0 (399.5) | 569.8 (494.8) | |
| Median | 45.5 | 467.3 | |
| Q1, Q3 | 0.0, 331.5 | 184.9, 777.8 | |
| Range | (0.0-2143.3) | (0.0-2200.0) | |
| MLANA_AVG_NORM | | | 0.1823 |
| N | 73 | 54 | |
| Mean (SD) | 3596.0 (3671.3) | 4865.4 (4966.1) | |
| Median | 2446.8 | 2803.5 | |
| Q1, Q3 | 950.9, 5019.4 | 1210.7, 6773.0 | |
| Range | (14.0-17180.3) | (62.8-19672.1) | |
| TYR_AVG_NORM | | | 0.0040 |
| N | 73 | 54 | |
| Mean (SD) | 349.7 (301.8) | 839.8 (996.3) | |
| Median | 254.3 | 515.1 | |
| Q1, Q3 | 119.5, 527.5 | 161.0, 1244.9 | |
| Range | (0.0-1169.8) | (2.0-5500.0) | |

TABLE C-continued

Comparison of gene expression between benign and malignant

|  | Benign (N = 73) | Malignant (N = 54) | p value |
|---|---|---|---|
| POSTN_AVG_NORM |  |  | 0.0001 |
| N | 73 | 54 |  |
| Mean (SD) | 1138.7 (2155.7) | 1933.9 (2318.1) |  |
| Median | 191.6 | 1252.0 |  |
| Q1, Q3 | 0.0, 1449.9 | 397.4, 2457.4 |  |
| Range | (0.0-11078.1) | (0.0-11193.2) |  |
| FBLN2_AVG_NORM |  |  | <0.0001 |
| N | 73 | 54 |  |
| Mean (SD) | 2.1 (17.3) | 26.5 (42.2) |  |
| Median | 0.0 | 0.0 |  |
| Q1, Q3 | 0.0, 0.0 | 0.0, 48.8 |  |
| Range | (0.0-148.2) | (0.0-150.9) |  |

TABLE D

Comparison of gene expression between benign and malignant

|  | Benign (N = 73) | Malignant (N = 54) | p value |
|---|---|---|---|
| CXCL1_AVG_NORM01 |  |  | <0.0001 |
| Zero | 58 (79.5%) | 12 (22.2%) |  |
| >0 | 15 (20.5%) | 42 (77.8%) |  |
| CSF2_AVG_NORM01 |  |  | 0.0398 |
| Zero | 15 (20.5%) | 20 (37.0%) |  |
| >0 | 58 (79.5%) | 34 (63.0%) |  |
| CCL2_AVG_NORM01 |  |  | <0.0001 |
| Zero | 53 (72.6%) | 12 (22.2%) |  |
| >0 | 20 (27.4%) | 42 (77.8%) |  |
| IL8_AVG_NORM01 |  |  | <0.0001 |
| Zero | 63 (86.3%) | 10 (18.5%) |  |
| >0 | 10 (13.7%) | 44 (81.5%) |  |
| IL6_AVG_NORM01 |  |  | <0.0001 |
| Zero | 65 (89.0%) | 13 (24.1%) |  |
| >0 | 8 (11.0%) | 41 (75.9%) |  |
| ITGA5_AVG_NORM01 |  |  | <0.0001 |
| Zero | 73 (100.0%) | 38 (70.4%) |  |
| >0 | 0 (0.0%) | 16 (29.6%) |  |
| ITGA3_AVG_NORM01 |  |  | <0.0001 |
| Zero | 72 (98.6%) | 13 (24.1%) |  |
| >0 | 1 (1.4%) | 41 (75.9%) |  |
| ITGA2_AVG_NORM01 |  |  | 0.0007 |
| Zero | 73 (100.0%) | 46 (85.2%) |  |
| >0 | 0 (0.0%) | 8 (14.8%) |  |
| ITGAV_AVG_NORM01 |  |  | <0.0001 |
| Zero | 71 (97.3%) | 24 (44.4%) |  |
| >0 | 2 (2.7%) | 30 (55.6%) |  |
| ITGB3_AVG_NORM01 |  |  | <0.0001 |
| Zero | 73 (100.0%) | 30 (55.6%) |  |
| >0 | 0 (0.0%) | 24 (44.4%) |  |
| ITGB1_AVG_NORM01 |  |  | <0.0001 |
| Zero | 64 (87.7%) | 11 (20.4%) |  |
| >0 | 9 (12.3%) | 43 (79.6%) |  |
| FN1_AVG_NORM01 |  |  | <0.0001 |
| Zero | 69 (94.5%) | 2 (3.7%) |  |
| >0 | 4 (5.5%) | 52 (96.3%) |  |
| THBS1_AVG_NORM01 |  |  | <0.0001 |
| Zero | 73 (100.0%) | 24 (44.4%) |  |
| >0 | 0 (0.0%) | 30 (55.6%) |  |
| THBS2_AVG_NORM01 |  |  | <0.0001 |
| Zero | 67 (91.8%) | 23 (42.6%) |  |
| >0 | 6 (8.2%) | 31 (57.4%) |  |
| THBS4_AVG_NORM01 |  |  | <0.0001 |
| Zero | 58 (79.5%) | 15 (27.8%) |  |
| >0 | 15 (20.5%) | 39 (72.2%) |  |
| VCAN_AVG_NORM01 |  |  | <0.0001 |
| Zero | 71 (97.3%) | 16 (29.6%) |  |
| >0 | 2 (2.7%) | 38 (70.4%) |  |
| BGAN_AVG_NORM01 |  |  | <0.0001 |
| Zero | 42 (57.5%) | 7 (13.0%) |  |
| >0 | 31 (42.5%) | 47 (87.0%) |  |
| SPP1_AVG_NORM01 |  |  | <0.0001 |
| Zero | 73 (100.0%) | 12 (22.2%) |  |
| >0 | 0 (0.0%) | 42 (77.8%) |  |
| TNC_AVG_NORM01 |  |  | <0.0001 |
| Zero | 60 (82.2%) | 3 (5.6%) |  |
| >0 | 13 (17.8%) | 51 (94.4%) |  |
| SPARC_AVG_NORM01 |  |  | <0.0001 |
| Zero | 57 (78.1%) | 13 (24.1%) |  |
| >0 | 16 (21.9%) | 41 (75.9%) |  |
| AGRN_AVG_NORM01 |  |  | <0.0001 |
| Zero | 59 (80.8%) | 5 (9.3%) |  |
| >0 | 14 (19.2%) | 49 (90.7%) |  |
| CTGF_AVG_NORM01 |  |  | <0.0001 |
| Zero | 72 (98.6%) | 21 (38.9%) |  |
| >0 | 1 (1.4%) | 33 (61.1%) |  |
| CYR61_AVG_NORM01 |  |  | <0.0001 |
| Zero | 56 (76.7%) | 9 (16.7%) |  |
| >0 | 17 (23.3%) | 45 (83.3%) |  |
| LAMA3_AVG_NORM01 |  |  | 0.0003 |
| Zero | 72 (98.6%) | 43 (79.6%) |  |
| >0 | 1 (1.4%) | 11 (20.4%) |  |
| LAMC1_AVG_NORM01 |  |  | <0.0001 |
| Zero | 73 (100.0%) | 24 (44.4%) |  |
| >0 | 0 (0.0%) | 30 (55.6%) |  |
| LAMB1_AVG_NORM01 |  |  | <0.0001 |
| Zero | 66 (90.4%) | 22 (40.7%) |  |
| >0 | 7 (9.6%) | 32 (59.3%) |  |
| LAMA1_AVG_NORM01 |  |  | <0.0001 |
| Zero | 57 (78.1%) | 16 (29.6%) |  |
| >0 | 16 (21.9%) | 38 (70.4%) |  |
| LAMC2_AVG_NORM01 |  |  | 0.0003 |
| Zero | 73 (100.0%) | 45 (83.3%) |  |
| >0 | 0 (0.0%) | 9 (16.7%) |  |
| LAMB3_AVG_NORM01 |  |  | 0.0061 |
| Zero | 45 (61.6%) | 20 (37.0%) |  |
| >0 | 28 (38.4%) | 34 (63.0%) |  |
| COL1A1_AVG_NORM01 |  |  | <0.0001 |
| Zero | 60 (82.2%) | 17 (31.5%) |  |
| >0 | 13 (17.8%) | 37 (68.5%) |  |
| COL4A1_AVG_NORM01 |  |  | <0.0001 |
| Zero | 73 (100.0%) | 13 (24.1%) |  |
| >0 | 0 (0.0%) | 41 (75.9%) |  |
| COL18A1_AVG_NORM01 |  |  | <0.0001 |
| Zero | 64 (87.7%) | 18 (33.3%) |  |
| >0 | 9 (12.3%) | 36 (66.7%) |  |
| LOX_AVG_NORM01 |  |  | <0.0001 |
| Zero | 60 (82.2%) | 26 (48.1%) |  |
| >0 | 13 (17.8%) | 28 (51.9%) |  |
| LOXL1_AVG_NORM01 |  |  | <0.0001 |
| Zero | 72 (98.6%) | 23 (42.6%) |  |
| >0 | 1 (1.4%) | 31 (57.4%) |  |

TABLE D-continued

Comparison of gene expression between benign and malignant

| | Benign (N = 73) | Malignant (N = 54) | p value |
|---|---|---|---|
| LOXL2_AVG_NORM01 | | | <0.0001 |
| Zero | 70 (95.9%) | 19 (35.2%) | |
| >0 | 3 (4.1%) | 35 (64.8%) | |
| LOXL3_AVG_NORM01 | | | <0.0001 |
| Zero | 69 (94.5%) | 10 (18.5%) | |
| >0 | 4 (5.5%) | 44 (81.5%) | |
| LOXL4_AVG_NORM01 | | | 0.0006 |
| Zero | 53 (72.6%) | 23 (42.6%) | |
| >0 | 20 (27.4%) | 31 (57.4%) | |
| PLOD1_AVG_NORM01 | | | <0.0001 |
| Zero | 59 (80.8%) | 12 (22.2%) | |
| >0 | 14 (19.2%) | 42 (77.8%) | |
| PLOD2_AVG_NORM01 | | | <0.0001 |
| Zero | 59 (80.8%) | 10 (18.5%) | |
| >0 | 14 (19.2%) | 44 (81.5%) | |
| PLOD3_AVG_NORM01 | | | <0.0001 |
| Zero | 66 (90.4%) | 11 (20.4%) | |
| >0 | 7 (9.6%) | 43 (79.6%) | |
| PCOLCE2_AVG_NORM01 | | | 0.0002 |
| Zero | 66 (90.4%) | 34 (63.0%) | |
| >0 | 7 (9.6%) | 20 (37.0%) | |
| PCOLCE_AVG_NORM01 | | | 0.0036 |
| Zero | 42 (57.5%) | 17 (31.5%) | |
| >0 | 31 (42.5%) | 37 (68.5%) | |
| PTK2_AVG_NORM01 | | | <0.0001 |
| Zero | 67 (91.8%) | 16 (29.6%) | |
| >0 | 6 (8.2%) | 38 (70.4%) | |
| CSRC_AVG_NORM01 | | | 0.0001 |
| Zero | 36 (49.3%) | 9 (16.7%) | |
| >0 | 37 (50.7%) | 45 (83.3%) | |
| CDKN1A_AVG_NORM01 | | | 0.0001 |
| Zero | 48 (65.8%) | 16 (29.6%) | |
| >0 | 25 (34.2%) | 38 (70.4%) | |
| CDKN2A_AVG_NORM01 | | | <0.0001 |
| Zero | 57 (78.1%) | 23 (42.6%) | |
| >0 | 16 (21.9%) | 31 (57.4%) | |
| TP53_AVG_NORM01 | | | <0.0001 |
| Zero | 59 (80.8%) | 16 (29.6%) | |
| >0 | 14 (19.2%) | 38 (70.4%) | |
| YAP_AVG_NORM01 | | | <0.0001 |
| Zero | 68 (93.2%) | 22 (40.7%) | |
| >0 | 5 (6.8%) | 32 (59.3%) | |
| TAZ_AVG_NORM01 | | | <0.0001 |
| Zero | 54 (74.0%) | 19 (35.2%) | |
| >0 | 19 (26.0%) | 35 (64.8%) | |
| MITF_AVG_NORM01 | | | <0.0001 |
| Zero | 26 (35.6%) | 2 (3.7%) | |
| >0 | 47 (64.4%) | 52 (96.3%) | |
| MLANA_AVG_NORM01 | | | |
| >0 | 73 (100.0%) | 54 (100.0%) | |
| TYR_AVG_NORM01 | | | 0.2202 |
| Zero | 2 (2.7%) | 0 (0.0%) | |
| >0 | 71 (97.3%) | 54 (100.0%) | |
| POSTN_AVG_NORM01 | | | <0.0001 |
| Zero | 32 (43.8%) | 4 (7.4%) | |
| >0 | 41 (56.2%) | 50 (92.6%) | |
| FBLN2_AVG_NORM01 | | | <0.0001 |
| Zero | 71 (97.3%) | 31 (57.4%) | |
| >0 | 2 (2.7%) | 23 (42.6%) | |

TABLE E

| | MM79_CN AVG per copy K14 | MM80_CN AVG per copy K14 | MM81_CN AVG per copy K14 | MM82_CN AVG per copy K14 | AVG per copy K14 | STDEV | % STDEV |
|---|---|---|---|---|---|---|---|
| KRT14_AVG_NORM | 1 | 1 | 1 | 1 | 1 | 0.000 | |
| KRT10_AVG_NORM | 2.209 | 2.229 | 2.92 | 3.015 | 2.593 | 0.434 | 17% |
| MITF_AVG_NORM | 0.021 | 0.018 | 0.016 | 0.015 | 0.018 | 0.003 | 15% |
| MLANA_AVG_NORM | 0.021 | 0.018 | 0.016 | 0.015 | 0.018 | 0.003 | 15% |
| TYR_AVG_NORM | 0.004 | 0.002 | 0.002 | 0.001 | 0.002 | 0.001 | 56% |
| PMEL_AVG_NORM | 0.025 | 0.027 | 0.03 | 0.018 | 0.025 | 0.005 | 20% |
| FN1_AVG_NORM | 0.077 | 0.065 | 0.035 | 0.042 | 0.055 | 0.020 | 36% |
| SPARC_AVG_NORM | 1.294 | 1.143 | 0.568 | 1.707 | 1.178 | 0.471 | 40% |
| AGRN_AVG_NORM | 0.004 | 0.006 | 0.003 | 0.002 | 0.004 | 0.002 | 46% |
| THBS1_AVG_NORM | 0.064 | 0.015 | 0.018 | 0.005 | 0.026 | 0.026 | 103% |
| THBS2_AVG_NORM | 0.366 | 0.061 | 0.104 | 0.057 | 0.147 | 0.148 | 100% |
| THBS4_AVG_NORM | 0.018 | 0.006 | 0.005 | 0.001 | 0.008 | 0.007 | 98% |
| VCAN_AVG_NORM | 0.095 | 0.034 | 0.04 | 0.027 | 0.049 | 0.031 | 64% |
| BGAN_AVG_NORM | 0.015 | 0.027 | 0.014 | 0.015 | 0.018 | 0.006 | 35% |
| COL1A1_AVG_NORM | 1.695 | 3.44 | 0.689 | 6.695 | 3.130 | 2.635 | 84% |
| COL4A1_AVG_NORM | 0.069 | 0.026 | 0.03 | 0.016 | 0.035 | 0.023 | 66% |
| COL4A2_AVG_NORM | 0.115 | 0.042 | 0.041 | 0.004 | 0.051 | 0.046 | 92% |
| COL18A1_AVG_NORM | 0.015 | 0.009 | 0.005 | 0.002 | 0.008 | 0.006 | 73% |
| CTGF_AVG_NORM | 0.012 | 0.008 | 0.016 | 0.004 | 0.010 | 0.005 | 52% |
| LOX_AVG_NORM | 0.029 | 0.021 | 0.028 | 0.021 | 0.025 | 0.004 | 18% |
| LOXL1_AVG_NORM | 0.015 | 0.009 | 0.016 | 0.015 | 0.014 | 0.003 | 23% |
| LOXL2_AVG_NORM | 0.016 | 0.011 | 0.008 | 0.006 | 0.010 | 0.004 | 42% |
| LOXL3_AVG_NORM | 0.003 | 0.002 | 0.002 | 0.001 | 0.002 | 0.001 | 41% |
| LOXL4_AVG_NORM | 0.02 | 0.004 | 0.003 | 0.001 | 0.007 | 0.009 | 125% |
| PLOD2_AVG_NORM | 0.018 | 0.014 | 0.007 | 0.001 | 0.010 | 0.008 | 75% |
| PLOD1_AVG_NORM | 0.069 | 0.053 | 0.026 | 0.017 | 0.041 | 0.024 | 58% |
| SPP1_AVG_NORM | 0.092 | 0.002 | 0.007 | 0 | 0.025 | 0.045 | 177% |
| TNC_AVG_NORM | 0.025 | 0.02 | 0.027 | 0.013 | 0.021 | 0.006 | 29% |
| PCOLCE2_AVG_NORM | 0.011 | 0.001 | 0.006 | 0 | 0.005 | 0.005 | 113% |
| PCOLCE_AVG_NORM | 0.028 | 0.049 | 0.032 | 0.04 | 0.037 | 0.009 | 25% |
| PLOD3_AVG_NORM | 0.03 | 0.006 | 0.007 | 0.002 | 0.011 | 0.013 | 113% |
| ITGB3_AVG_NORM | 0.03 | 0.006 | 0.007 | 0.002 | 0.011 | 0.013 | 113% |
| ITGB1_AVG_NORM | 0.164 | 0.054 | 0.074 | 0.038 | 0.083 | 0.056 | 68% |
| FBLN2_AVG_NORM | 0.049 | 0.022 | 0.02 | 0.016 | 0.027 | 0.015 | 56% |
| CYR61_AVG_NORM | 0.006 | 0.002 | 0.003 | 0 | 0.003 | 0.003 | 91% |

TABLE E-continued

| | MM79_CN AVG per copy K14 | MM80_CN AVG per copy K14 | MM81_CN AVG per copy K14 | MM82_CN AVG per copy K14 | AVG per copy K14 | STDEV | % STDEV |
|---|---|---|---|---|---|---|---|
| ITGA5_AVG_NORM | 0.011 | 0.005 | 0.007 | 0.003 | 0.007 | 0.003 | 53% |
| ITGA3_AVG_NORM | 0.016 | 0.008 | 0.006 | 0.008 | 0.010 | 0.004 | 47% |
| ITGA2_AVG_NORM | 0.08 | 0.034 | 0.019 | 0.084 | 0.054 | 0.033 | 60% |
| ITGAV_AVG_NORM | 0.013 | 0.005 | 0.003 | 0.003 | 0.006 | 0.005 | 79% |
| CSRC_AVG_NORM | 0.006 | 0.003 | 0.005 | 0.001 | 0.004 | 0.002 | 59% |
| PTK2_AVG_NORM | 0.035 | 0.02 | 0.011 | 0.009 | 0.019 | 0.012 | 63% |
| POSTN_AVG_NORM | 0.077 | 0.092 | 0.117 | 0.193 | 0.120 | 0.052 | 43% |
| YAP_AVG_NORM | 0.079 | 0.029 | 0.033 | 0.031 | 0.043 | 0.024 | 56% |
| CXCL1_AVG_NORM | 0.002 | 0 | 0 | 0 | 0.001 | 0.001 | 200% |
| CSF2_AVG_NORM | 0.002 | 0 | 0 | 0 | 0.001 | 0.001 | 200% |
| CCL2_AVG_NORM | 0.039 | 0.018 | 0.013 | 0.008 | 0.020 | 0.014 | 70% |
| IL8_AVG_NORM | 0.003 | 0 | 0.001 | 0 | 0.001 | 0.001 | 141% |
| IL6_AVG_NORM | 0.001 | 0 | 0 | 0 | 0.000 | 0.001 | 200% |
| LAMA3_AVG_NORM | 0.038 | 0.012 | 0.021 | 0.011 | 0.021 | 0.013 | 61% |
| TP53_AVG_NORM | 0.08 | 0.04 | 0.039 | 0.052 | 0.053 | 0.019 | 36% |
| CDKN1A_AVG_NORM | 0.057 | 0.029 | 0.037 | 0.014 | 0.034 | 0.018 | 52% |
| CDKN2A_AVG_NORM | 0.003 | 0.001 | 0.001 | 0 | 0.001 | 0.001 | 101% |
| TAZ_AVG_NORM | 0.026 | 0.008 | 0.008 | 0.003 | 0.011 | 0.010 | 90% |
| LAMC1_AVG_NORM | 0.062 | 0.013 | 0.016 | 0.008 | 0.025 | 0.025 | 101% |
| LAMB1_AVG_NORM | 0.046 | 0.019 | 0.026 | 0.008 | 0.025 | 0.016 | 65% |
| LAMA1_AVG_NORM | 0.007 | 0 | 0.001 | 0 | 0.002 | 0.003 | 168% |
| LAMC2_AVG_NORM | 0.034 | 0.009 | 0.012 | 0.016 | 0.018 | 0.011 | 63% |
| LAMB3_AVG_NORM | 0.042 | 0.016 | 0.026 | 0.017 | 0.025 | 0.012 | 48% |
| PLAT_AVG_NORM | 0.032 | 0.02 | 0.034 | 0.04 | 0.032 | 0.001 | 27% |
| CSK_AVG_NORM | 0.027 | 0.034 | 0.021 | 0.041 | 0.031 | 0.001 | 28% |
| GDF15_AVG_NORM | 0.029 | 0.019 | 0.033 | 0.019 | 0.025 | 0.001 | 28% |
| FARP1_AVG_NORM | 0.019 | 0.029 | 0.022 | 0.031 | 0.025 | 0.001 | 22% |
| ARPC1B_AVG_NORM | 0.015 | 0.03 | 0.042 | 0.018 | 0.026 | 0.012 | 47% |
| NES_AVG_NORM | 0.114 | 0.125 | 0.112 | 0.084 | 0.109 | 0.017 | 16% |
| NTRK3_AVG_NORM | 0.021 | 0.025 | 0.022 | 0.033 | 0.025 | 0.001 | 25% |
| SNX17_AVG_NORM | 0.112 | 0.099 | 0.089 | 0.123 | 0.106 | 0.015 | 14% |
| L1CAM_AVG_NORM | 0.017 | 0.04 | 0.01 | 0.024 | 0.023 | 0.013 | 56% |
| CD44_AVG_NORM | 0.112 | 0.089 | 0.09 | 0.123 | 0.104 | 0.017 | 16% |

The results provided herein demonstrate the development of a method for determining absolute levels (copy numbers) of genes of interest (e.g., FN-associated genes) from paraffin-embedded tissue by generating a highly defined internal standard that can be regenerated indefinitely. This standardization approach can allow for the comparison of results from independent experiments and thus, allows for extensive validation. The RT-PCR not only produced strong signals from highly degraded RNA due to FFPE embedding, but also was amendable to high-throughput analysis and was highly cost effective. While the methods provided herein were validated for melanoma, these methods are likely applicable to other human cancers. The results provided herein also demonstrate the discrimination between benign and malignant pigmented lesions based on multiple markers.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A set of kit components within a kit for identifying a malignant skin lesion in a subject when used together with a set of reagents comprising:
   (a) primer pairs for determining, within a test sample taken from the subject, the expression level of marker genes PLAT, ITGB3, and IL8 to obtain a measured expression level of the marker genes for the test sample, and
   (b) a primer pair for determining, within the test sample, the expression level of marker gene GDF15, to obtain a measured expression level of the marker gene GDF15 for the test sample, wherein the set of kit components comprises:

a control nucleic acid for each of the primer pairs, wherein each control nucleic acid comprises a target nucleic acid for one of the primer pairs configured to obtain a standard curve for the primer pair, and wherein each of the control nucleic acids is complementary DNA (cDNA) specific for cDNA and not specific for genomic DNA.

2. A set of kit components within a kit comprising:
(i) a first composition comprising a control nucleic acid for a primer pair for determining, within a test sample, the expression level of marker gene GDF15, said control nucleic acid comprising a target nucleic acid for the primer pair configured to obtain a standard curve for the primer pair;
(ii) a second composition comprising a control nucleic acid for a primer pair for determining, within the test sample, the expression level of marker gene PLAT, said control nucleic acid comprising a target nucleic acid for the primer pair configured to obtain a standard curve for the primer pair;
(iii) a third composition comprising a control nucleic acid for a primer pair for determining, within the test sample, the expression level of marker gene ITGB3, said control nucleic acid comprising a target nucleic acid for the primer pair configured to obtain a standard curve for the primer pair; and
(iv) a fourth composition comprising a control nucleic acid for a primer pair for determining, within the test sample, the expression level of marker gene IL8, said control nucleic acid comprising a target nucleic acid for the primer pair configured to obtain a standard curve for the primer pair,
wherein each of the control nucleic acids is complementary DNA (cDNA) specific for cDNA and not specific for genomic DNA.

* * * * *